US012183437B2

(12) United States Patent
Tsao et al.

(10) Patent No.: US 12,183,437 B2
(45) Date of Patent: *Dec. 31, 2024

(54) SEQUENCING OUTPUT DETERMINATION AND ANALYSIS WITH TARGET-ASSOCIATED MOLECULES IN QUANTIFICATION ASSOCIATED WITH BIOLOGICAL TARGETS

(71) Applicant: BillionToOne, Inc., Menlo Park, CA (US)

(72) Inventors: David Tsao, San Carlos, CA (US); Oguzhan Atay, Menlo Park, CA (US)

(73) Assignee: BILLIONTOONE, INC., Menlo Park, CA (US)

( * ) Notice: Subject to any disclaimer, the term of this patent is extended or adjusted under 35 U.S.C. 154(b) by 136 days.

This patent is subject to a terminal disclaimer.

(21) Appl. No.: 17/816,662

(22) Filed: Aug. 1, 2022

(65) Prior Publication Data

US 2023/0197202 A1 Jun. 22, 2023

Related U.S. Application Data

(63) Continuation of application No. 16/056,112, filed on Aug. 6, 2018, now Pat. No. 11,430,543.

(60) Provisional application No. 62/541,565, filed on Aug. 4, 2017.

(51) Int. Cl.
*C12P 19/34* (2006.01)
*C12Q 1/6851* (2018.01)
*C12Q 1/6869* (2018.01)
*G16B 40/00* (2019.01)
*C12Q 1/6883* (2018.01)
*C12Q 1/6886* (2018.01)

(52) U.S. Cl.
CPC ........... *G16B 40/00* (2019.02); *C12Q 1/6851* (2013.01); *C12Q 1/6869* (2013.01); *C12Q 1/6883* (2013.01); *C12Q 1/6886* (2013.01)

(58) Field of Classification Search
CPC .................................................. C12Q 1/6869
See application file for complete search history.

(56) References Cited

U.S. PATENT DOCUMENTS

| | | | |
|---|---|---|---|
| 8,105,422 B2 | 1/2012 | Betting et al. | |
| 8,195,415 B2 | 6/2012 | Fan et al. | |
| 8,467,976 B2 | 6/2013 | Lo et al. | |
| 8,688,388 B2 | 4/2014 | Dzakula et al. | |
| 8,877,442 B2 | 11/2014 | Quake et al. | |
| 9,512,480 B2 | 12/2016 | Lo et al. | |
| 9,944,973 B2 | 4/2018 | Willey et al. | |
| 11,519,024 B2 * | 12/2022 | Landry | C12Q 1/6869 |
| 11,646,100 B2 * | 5/2023 | Tsao | C12N 15/10 |
| | | | 702/19 |
| 2007/0009884 A1 | 1/2007 | Stoughton et al. | |
| 2007/0092869 A1 | 4/2007 | Fulmer Smentek et al. | |
| 2008/0124712 A1 | 5/2008 | Hantash et al. | |
| 2010/0323352 A1 | 12/2010 | Lo et al. | |
| 2011/0033861 A1 | 2/2011 | Wu et al. | |
| 2011/0201507 A1 | 8/2011 | Rava et al. | |
| 2012/0010085 A1 | 1/2012 | Rava et al. | |
| 2012/0021919 A1 | 1/2012 | Scholl et al. | |
| 2012/0270739 A1 | 10/2012 | Rava et al. | |
| 2013/0022973 A1 | 1/2013 | Hansen et al. | |
| 2013/0130923 A1 | 5/2013 | Ehrich et al. | |
| 2014/0195164 A1 | 7/2014 | Lo et al. | |
| 2015/0099266 A1 | 4/2015 | Samuels et al. | |
| 2015/0133391 A1 | 5/2015 | de Vlaminick et al. | |
| 2015/0152474 A1 | 6/2015 | Pawlowski et al. | |
| 2015/0284783 A1 | 10/2015 | Canton | |
| 2016/0040229 A1 | 2/2016 | Talasaz et al. | |
| 2016/0130649 A1 | 5/2016 | Xie et al. | |
| 2016/0187292 A1 | 6/2016 | Yoshida et al. | |
| 2016/0195164 A1 | 7/2016 | Verhoog et al. | |
| 2016/0222391 A1 | 8/2016 | Krieg et al. | |
| 2016/0251719 A1 | 9/2016 | Umbarger | |
| 2016/0319345 A1 | 11/2016 | Gnerre et al. | |

(Continued)

FOREIGN PATENT DOCUMENTS

| | | |
|---|---|---|
| CN | 104640997 A | 5/2015 |
| CN | 105164279 A | 12/2015 |

(Continued)

OTHER PUBLICATIONS

Applied Biosystems, "Application Note: Detection and Quantification of Sequence Variants from Sanger Sequencing Traces: Determination of minor alleles by analyzing peak height data," 2013, pp. 1-13.
Brinkman, E.K. et al., "Easy quantitative assessment of genome editing by sequence trace decomposition," Nucleic Acids Research, vol. 42, Issue 22, Oct. 9, 2014, pp. 1-8.
Carr, I. M. et al., "Inferring relative proportions of DNA variants from sequencing electropherograms", Bioinformatics, vol. 25, Issue 24. Oct. 9, 2009, pp. 3244-3250.
Curci, P. L. et al., "How a Small Double-Stranded Trick Can Mislead Sanger Sequencing.", Journal of Biomolecular Techniques, vol. 26, Issue 3, Sep. 2015, pp. 80-82.
European Patent Office, Extended European Search Report and Opinion, EP Patent Application No. 18841428.8, Mar. 31, 2021, 8 pages.
International Preliminary Report on Patentability for PCT/US18/45434, Jul. 7, 2020, 8 pages.

(Continued)

*Primary Examiner* — Kenneth R Horlick
(74) *Attorney, Agent, or Firm* — Fenwick & West LLP

(57) ABSTRACT

Embodiments of a method and/or system can include generating a set of target-associated molecules (e.g., spike-in molecules) associated with one or more biological targets; generating one or more spike-in mixtures based on processing the set of target-associated molecules with one or more samples including the one or more biological targets; performing one or more Sanger sequencing operations on the one or more spike-in mixtures; determining one or more abundance metrics based on chromatogram-related outputs from the one or more Sanger sequencing operations; and/or facilitating characterization of one or more medical conditions based on the one or more abundance metrics.

18 Claims, 21 Drawing Sheets

Specification includes a Sequence Listing.

(56) References Cited

U.S. PATENT DOCUMENTS

| | | | |
|---|---|---|---|
| 2017/0175187 | A1 | 6/2017 | Rabinowitz et al. |
| 2017/0275691 | A1 | 9/2017 | Christians et al. |
| 2017/0327869 | A1 | 11/2017 | Schutz et al. |
| 2018/0023125 | A1 | 1/2018 | Talasaz et al. |
| 2021/0292829 | A1* | 9/2021 | Brown .................. C12Q 1/6853 |

FOREIGN PATENT DOCUMENTS

| | | |
|---|---|---|
| JP | 2016-511632 A | 4/2016 |
| JP | 2017-060479 A | 3/2017 |
| WO | WO 00/68410 A1 | 11/2000 |
| WO | WO 2006/011738 A1 | 2/2006 |
| WO | WO 2011/091046 A1 | 7/2011 |
| WO | WO 2011/156795 A1 | 12/2011 |
| WO | WO 2012/058316 A1 | 5/2012 |
| WO | WO 2012/129363 A1 | 9/2012 |
| WO | WO 2014/039556 A1 | 3/2014 |
| WO | WO 2014/082032 A1 | 5/2014 |
| WO | WO 2014/127484 A1 | 8/2014 |
| WO | WO 2016/094947 A1 | 6/2016 |
| WO | WO 2016/187655 A1 | 12/2016 |
| WO | WO 2017/165864 A1 | 9/2017 |
| WO | WO 2017/210372 A1 | 12/2017 |
| WO | WO 2018/031486 A1 | 2/2018 |

OTHER PUBLICATIONS

International Preliminary Report on Patentability for PCT/US2018/045394, Feb. 4, 2020, 6 pages.
International Preliminary Report on Patentability for PCT/US2018/045419, Feb. 4, 2020, 11 pages.
International Search Report and the Written Opinion, PCT Application No. PCT/US19/45331, Oct. 25, 2019, 7 pages.
International Search Report and the Written Opinion, PCT Application No. PCT/US191014340, Mar. 29, 2019, 22 pages.
International Search Report and the Written Opinion, PCT Application No. PCT/US18/45419, Dec. 21, 2018, 15 pages.
International Search Report and Written Opinion, PCT Application No. PCT/US2018/045434, Nov. 29, 2018, 11 pages.
International Search Report and Written Opinion, PCT Application No. PCT/US2018/045394, Oct. 10, 2018, 8 pages.
Japan Patent Office, Office Action, JP Patent Application No. 2020-504691, Mar. 30, 2021, six pages.
Kaboev, O. K. et al., "PCR hot start using primers with the structure of molecular beacons {hairpin-like structure}", Nucleic Acids Research, vol. 28, No. 21, e94, Nov. 1, 2000, pp. 1-2.
Lun, M. F. et al., "Noninvasive prenatal diagnosis of monogenic diseases by digital size selection and relative mutation dosage on DNA in maternal plasma.", PNAS, vol. 105, No. 50, Dec. 16, 2008, pp. 19920-19925.
Quail, M. A. et al., "SASI-Seq: sample assurance Spike-Ins, and highly differentiating 384 barcoding for Illumina sequencing.", BMC Genomics, 15, Dec. 2014, pp. 1-12.
Silas, S. et al., "Direct CRISPR spacer acquisition from RNA by a natural reverse transcriptase-Cas1 fusion protein.", Science, 351(6276), aad4234, Feb. 26, 2017, pp. 1-31.
Sinha, R. et al., "Index Switching Causes "Spreading-of-Signal" Among Multiplexed Samples in Illumina HiSeq 4000 DNA Sequencing.", BioRxiv, Apr. 9, 2017, pp. 1-29.
Tourlousse, D.M. et al., "Synthetic spike-in standards for high-throughput 16S rRNA gene amplicon sequencing," Nucleic Acids Research, vol. 45, No. 4, e23, Feb. 28, 2016, pp. 1-14 and supplementary data.
Tsao, D.S. et al., "A novel high-throughput molecular counting method with single base-pair resolution enables accurate single-gene NIPT," Scientific Reports, 9(1), Oct. 7, 2019, pp. 1-14.
Yan, T.Z. et al., "Reliable detection of paternal SNPs within deletion breakpoints for non-invasive prenatal exclusion of homozygous α0-thalassemia in maternal plasma.", PLoS One, vol. 6, No. 9, e24779, Sep. 29, 2011, pp. 1-9.
Zhidkov, I. et al., "CHILD: a new tool for detecting low-abundance insertions and deletions in standard sequence traces," Nucleic Acids Research, vol. 39, No. 4, Jan. 27, 2011, pp. 1-8.
Chinese Patent Office, Office Action, Chinese Patent Application No. 201880057463.8, Feb. 24, 2023, 10 pages.
United States Office Action, U.S. Appl. No. 16/056,112, Dec. 7, 2021, 31 pages.
Brazilian National Institute of Industrial Property, Office Action and Search Report with English Translation, Brazilian Patent Application No. BR 112020002260-8, Feb. 27, 2024, 8 pages.

* cited by examiner

| DNA Oligonucleotide Name | Sequence |
|---|---|
| chr21:14439004_PCR2_FP | 5'-CGA CGC TCT TCC GAT CTA AAG GGC CAG GCC TTT TCC AGT AT-3' |
| chr21:14439076_PCR2_RP_hp | 5'-GAA TTA CGT ATG TAA TTC ACT GAC GCT AGT GCA TCA TTC TTC AAG GGA CAG ACA ACG CTC-3' |
| chr21:14439004_PCR1_FP | 5'-GGC CAG GCC TTT TCC AGT AT-3' |
| chr21:14439076_PCR1_RP | 5'-TCA AGG GAC AGA CAA CGC TC-3' |

Design of PCR primers (capitalized) and spike-in for chr21:15811326-15811417.

>chr18:12340277+12340405 129bp
Target   ACCAGGTATCCATCATCCCACGTGGCAAAGGACTAGGTTATGCTCAGTATTTACCAAAAGAACAATACCTCTATACCAAAGAGCAGCTCTTGGATAGGATGTGTATGACTTTAGGTGGTCGAGTCTCTG
Spike-in ACCAGGTATCCATCATCCCACGTGGCAAAGGACTAGGTTATGCTCAGTATTTACCAAAAGAACAATACCTCTATACCAAAGAGCAGCCTGGTTTAGAGATGTGTATGACTTTAGGTGGTCGAGTCTCTG

FIGURE 11

SEQUENCE LISTING

```
Sequence total quantity: 15
SEQ ID NO: 1            moltype = DNA  length = 92
FEATURE                 Location/Qualifiers
source                  1..92
                        mol_type = other DNA
                        organism = Homo sapiens
SEQUENCE: 1
ggccaggcct tttccagtat ttacttattt tatggaaaaa ccaaacttta tcactagaca   60
caaaatttaa gtgagcgttg tctgtccctt ga                                 92

SEQ ID NO: 2            moltype = DNA  length = 89
FEATURE                 Location/Qualifiers
misc_feature            1..89
                        note = Synthetic construct
source                  1..89
                        mol_type = other DNA
                        organism = synthetic construct
SEQUENCE: 2
ggccaggcct tttccagtat ttacttttat ggaaaaacca aactttatca ctagacacaa   60
aatttaagtg agcgttgtct gtcccttga                                     89
```

```
SEQ ID NO: 3              moltype = DNA   length = 41
FEATURE                   Location/Qualifiers
misc_feature              1..41
                          note = Synthetic construct
source                    1..41
                          mol_type = other DNA
                          organism = synthetic construct
SEQUENCE: 3
cgacgctctt ccgatctaaa gggccaggcc ttttccagta t                41

SEQ ID NO: 4              moltype = DNA   length = 60
FEATURE                   Location/Qualifiers
misc_feature              1..60
                          note = Synthetic construct
source                    1..60
                          mol_type = other DNA
                          organism = synthetic construct
SEQUENCE: 4
gaattacgta tgtaattcac tgacgctagt gcatcattct tcaagggaca gacaacgctc  60

SEQ ID NO: 5              moltype = DNA   length = 20
FEATURE                   Location/Qualifiers
misc_feature              1..20
                          note = Synthetic construct
source                    1..20
                          mol_type = other DNA
                          organism = synthetic construct
SEQUENCE: 5
ggccaggcct tttccagtat                                        20

SEQ ID NO: 6              moltype = DNA   length = 20
FEATURE                   Location/Qualifiers
misc_feature              1..20
                          note = Synthetic construct
source                    1..20
                          mol_type = other DNA
                          organism = synthetic construct
SEQUENCE: 6
tcaagggaca gacaacgctc                                        20

SEQ ID NO: 7              moltype = DNA   length = 361
FEATURE                   Location/Qualifiers
misc_feature              1..361
                          note = Synthetic construct
source                    1..361
                          mol_type = other DNA
                          organism = synthetic construct
SEQUENCE: 7
gcctacactc tttccctaca cgacgctctt ccgatctaaa gggccaggcc ttttccagta   60
tttacttatt ttatggaaaa accaaacttt atcactagac acaaaattta agtgagcgtt  120
gtctgtccct tgaagaatga tgcactagcg tcagtgaatt acatacgtaa ttcactgacg  180
ctagtgcatc attcttcaag ggacagacaa cgctcactta aattttgtgt ctagtgataa  240
agtttggttt ttccataaaa taagtaaata ctggaaaagg cctggccctt tagatcggaa  300
gagcgtcgtg tagggaaaga gtgtaggcta tagtgtagat ctcggtggtc gccgtatcat  360
t                                                            361

SEQ ID NO: 8              moltype = DNA   length = 44
FEATURE                   Location/Qualifiers
source                    1..44
                          mol_type = other DNA
                          organism = Homo sapiens
SEQUENCE: 8
aaagaacaat acctctatac caaagagcag ctcttggata ggat             44

SEQ ID NO: 9              moltype = DNA   length = 44
FEATURE                   Location/Qualifiers
misc_feature              1..44
                          note = Synthetic construct
source                    1..44
                          mol_type = other DNA
                          organism = synthetic construct
SEQUENCE: 9
aaagaacaat acctctatac caaagagcag cctggtttag agat             44

SEQ ID NO: 10             moltype = DNA   length = 44
FEATURE                   Location/Qualifiers
misc_feature              1..44
                          note = Synthetic construct
```

```
source                  1..44
                        mol_type = other DNA
                        organism = synthetic construct
SEQUENCE: 10
aaagaacaat acctctatac caaagagcag cctttgttta agat             44

SEQ ID NO: 11           moltype = DNA  length = 129
FEATURE                 Location/Qualifiers
source                  1..129
                        mol_type = other DNA
                        organism = Homo sapiens
SEQUENCE: 11
accaggtatc catcatccca cgtggcaaag gactaggtta tgctcagtat ttaccaaaag   60
aacaatacct ctataccaaa gagcagctct tggataggat gtgtatgact ttaggtggtc  120
gagtctctg                                                         129

SEQ ID NO: 12           moltype = DNA  length = 129
FEATURE                 Location/Qualifiers
misc_feature            1..129
                        note = Synthetic construct
source                  1..129
                        mol_type = other DNA
                        organism = synthetic construct
SEQUENCE: 12
accaggtatc catcatccca cgtggcaaag gactaggtta tgctcagtat ttaccaaaag   60
aacaatacct ctataccaaa gagcagcctg gtttagagat gtgtatgact ttaggtggtc  120
gagtctctg                                                         129

SEQ ID NO: 13           moltype = DNA  length = 33
FEATURE                 Location/Qualifiers
misc_feature            1..33
                        note = Synthetic construct
source                  1..33
                        mol_type = other DNA
                        organism = synthetic construct
SEQUENCE: 13
tcagatcggg gccccctatg actccaaagg tta                          33

SEQ ID NO: 14           moltype = DNA  length = 33
FEATURE                 Location/Qualifiers
misc_feature            1..33
                        note = Synthetic construct
source                  1..33
                        mol_type = other DNA
                        organism = synthetic construct
SEQUENCE: 14
ttaccagaat atcttgaata tatggtaata aag                          33

SEQ ID NO: 15           moltype = DNA  length = 33
FEATURE                 Location/Qualifiers
misc_feature            1..33
                        note = Synthetic construct
source                  1..33
                        mol_type = other DNA
                        organism = synthetic construct
SEQUENCE: 15
cggaatccct cagcaaagtc tcaaaaagag gac                          33
```

SEQUENCING OUTPUT DETERMINATION AND ANALYSIS WITH TARGET-ASSOCIATED MOLECULES IN QUANTIFICATION ASSOCIATED WITH BIOLOGICAL TARGETS

CROSS-REFERENCE TO RELATED APPLICATIONS

This application is a continuation of U.S. application Ser. No. 16/056,112, filed Aug. 6, 2018, now U.S. Pat. No. 11,430,543, which claims the benefit of U.S. Provisional Application No. 62/541,565, filed on Aug. 4, 2017, each of which is incorporated herein in its entirety by reference.

SEQUENCE LISTING

The instant application contains a Sequence Listing which has been submitted via USPTO's Patent Center and is hereby incorporated by reference in its entirety. Said XML copy, created on Feb. 2, 2023, is named 53089-US-SequenceListing.xml and is 19,806 bytes in size.

TECHNICAL FIELD

This disclosure relates generally to the field of genomics.

BRIEF DESCRIPTION OF THE FIGURES

FIG. 11 includes a specific example of a target sequence and target-associated sequence (specific example of Target=SEO ID NO: 11: specific example of Spike-in =SEO ID NO: 12);

DESCRIPTION OF THE EMBODIMENTS

Figure 1A:
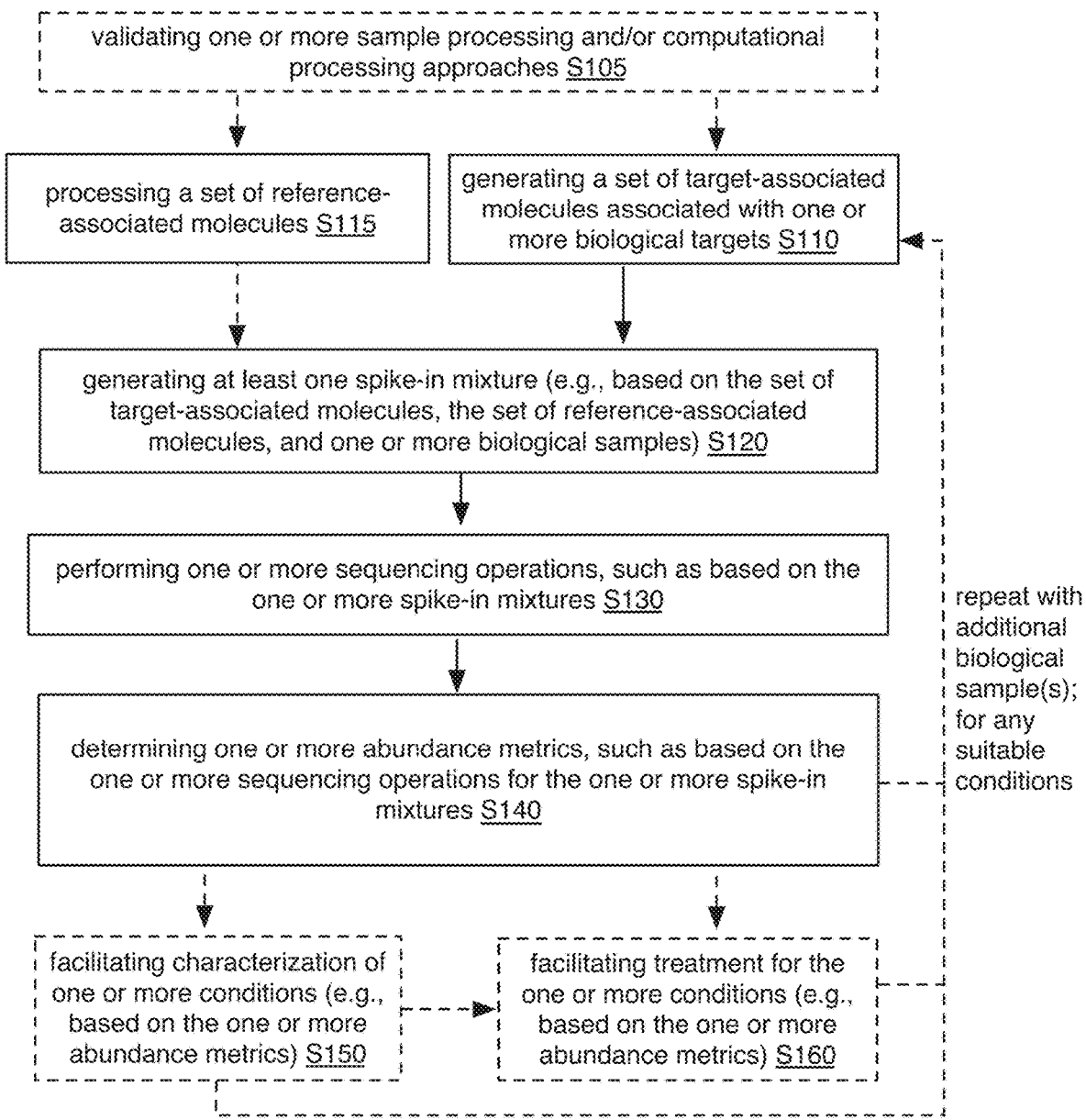
FIGS. 1A-1C include flowchart representations of variations of embodiments of a method.
Figure 1B:
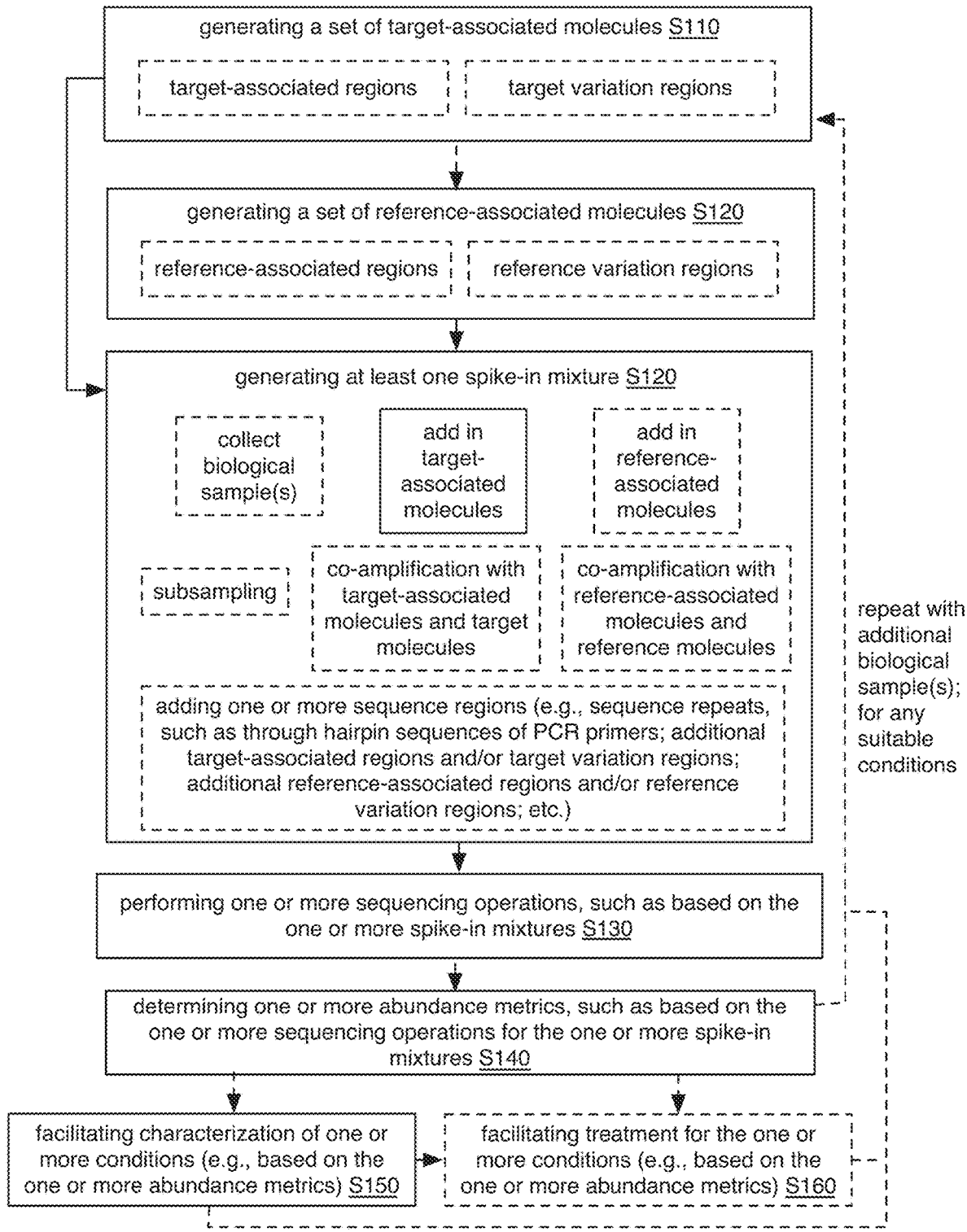
Figure 1C:
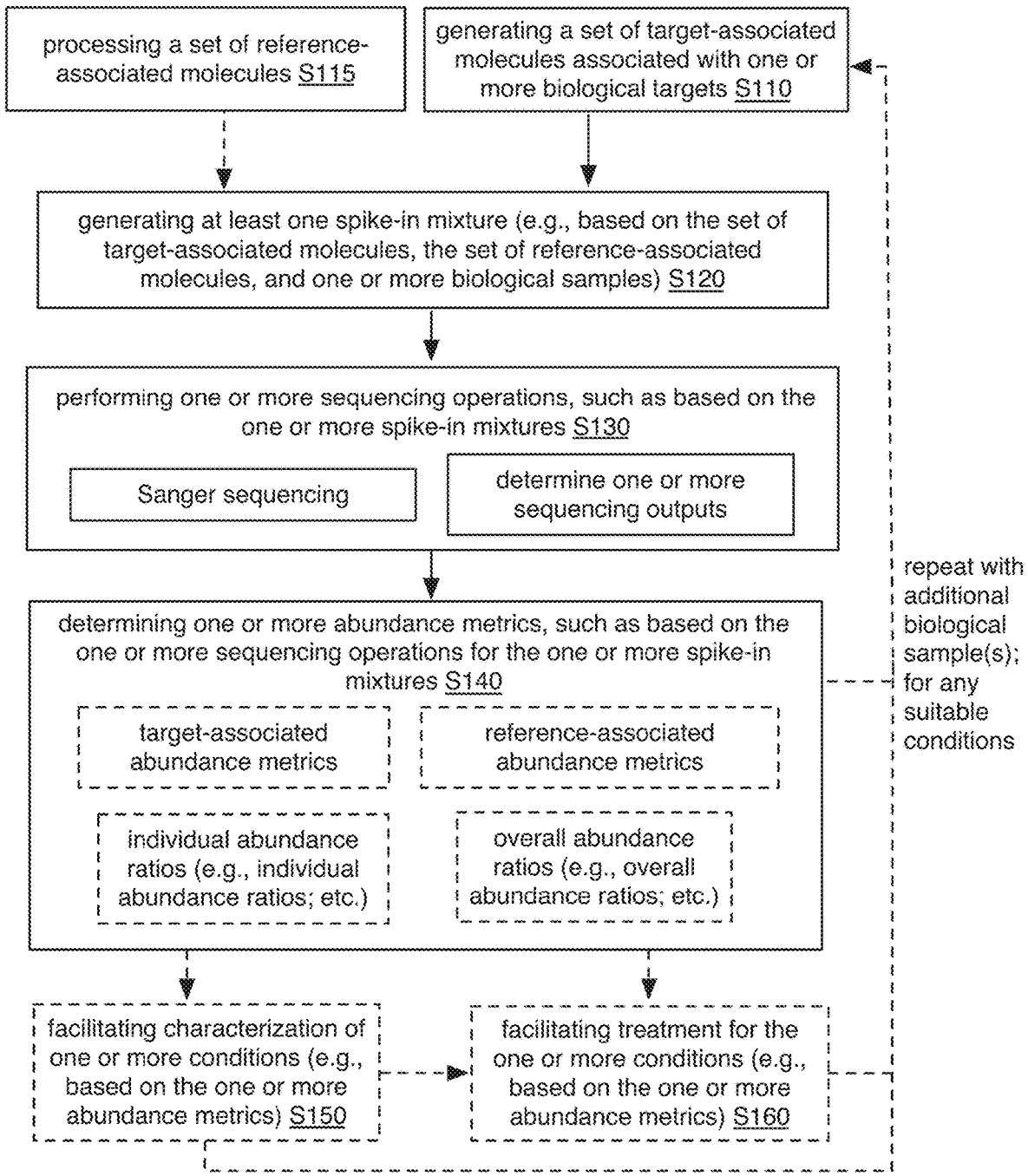
Figure 2:
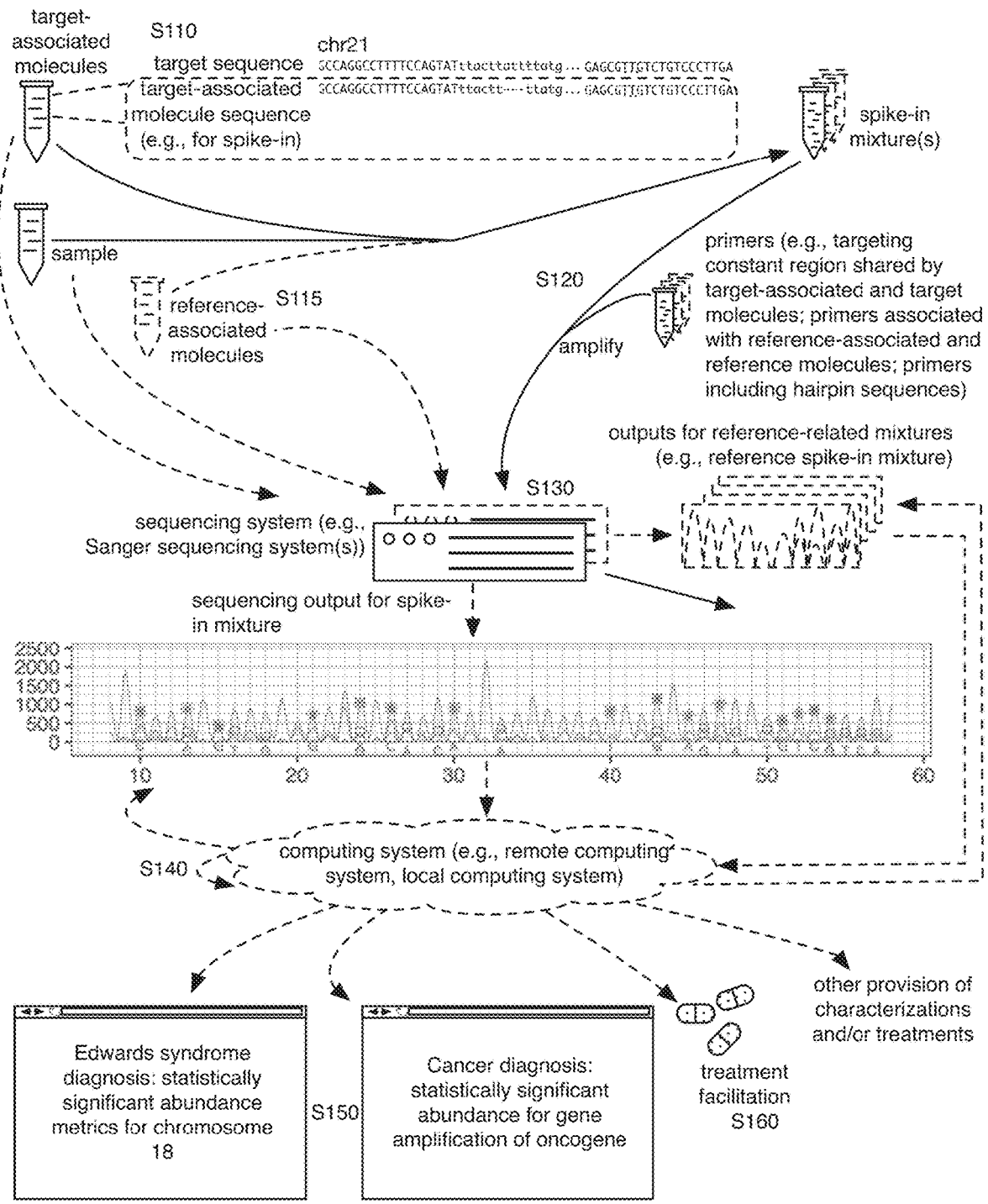
FIG. 2 includes a schematic representation of a variation of an embodiment of a method (specific example of target sequence=portion of SEO ID NO: 1: specific example of target-associated molecule sequence=portion of SEO ID NO: 2)

The following description of the embodiments (e.g., including variations of embodiments, examples of embodiments, specific examples of embodiments, other suitable variants, etc.) is not intended to be limited to these embodiments, but rather to enable any person skilled in the art to make and use.

1. Overview

As shown in FIGS. 1A-1C and 2, embodiments of a method 100 (e.g., for determining biological target abundance; for facilitating characterization of one or more conditions etc.) can include: generating a set of target-associated molecules (e.g., spike-in molecules, etc.) associated with one or more biological targets Silo; generating one or more spike-in mixtures S120 (e.g., based on processing the set of target-associated molecules with one or more samples, such as biological samples and/or synthetic samples, including the one or more biological targets, etc.), such as where the one or more spike-in mixtures can be configured to facilitate increased accuracy (e.g., though minimizing amplification biases, such as based on co-amplification of the target-associated molecules with the one or more biological targets; etc.) and/or increased deployability (e.g., through compatibility with sequencing technologies such as Sanger sequencing, etc.); performing one or more sequencing operations S130 (e.g., Sanger sequencing, etc.), such as based on the one or more spike-in mixtures; and/or determining one or more abundance metrics S140 (e.g., an abundance ratio of target molecules relative target-associated molecules; etc.), such as based on the one or more sequencing operations for the one or more spike-in mixtures (e.g., based on relative chromatogram peak intensities between endogenous bases and spike-in bases, etc.).

Additionally or alternatively, embodiments of the method 100 can include one or more of: processing a set of reference-associated molecules S115 (e.g., associated with reference molecules in the sample, where abundance metrics determined in relation to the set of reference-associated molecules can be compared to target-related abundance metrics for facilitating characterizations and/or treatments for one or more conditions; etc.); facilitating the characterization of one or more conditions S150, such as based on the one or more abundance metrics; facilitating treatment S160 (e.g., of the one or more conditions based on the one or more abundance metrics, etc.); and/or validating S105, such as validating one or more portions of embodiments of the method 100; and/or any other suitable process.

In a specific example, the method 100 (e.g., for facilitating prenatal diagnosis of a genetic disorder, such as one or more chromosomal disorders and/or single gene disorders, from a maternal sample associated with a pregnant woman, etc.) can include: generating a set of target-associated molecules including a target-associated sequence including: a target-associated region with sequence similarity to a target sequence region of a target sequence of a biological target, where the biological target is associated with the genetic disorder; and a target variation region with sequence dissimilarity to a sequence region of the target sequence; generating a co-amplified spike-in mixture based on co-amplifying the set of target-associated molecules and nucleic acid molecules from the maternal sample, where the nucleic acid molecules include the target sequence region; Sanger sequencing the co-amplified spike-in mixture to determine at least one chromatogram-related output (e.g., a chromatogram, peaks corresponding to bases, intensities of the peaks, etc.) including peaks associated with the target-associated region, the target sequence region of the biological target, the target variation region, and the sequence region of the biological target; determining a set of target-associated abundance ratios (and/or other suitable abundance metrics; etc.), where each target-associated abundance ratio, of the set of target-associated abundance ratios, corresponds to a different pair of a base of the target-associated sequence and a base of the target sequence (e.g., where the bases of the pair share a same base type; where the bases of the pair share different base types; etc.), where determining the set of target-associated abundance ratios includes, for each of the different pairs: determining a peak intensity metric (e.g., maximum intensity for the peak; overall intensity for the peak; etc.) for the base of the target-associated sequence of the pair, based on the at least one chromatogram-related output (e.g., based on intensity values for peaks, determined based on the Sanger sequencing; etc.); determining a peak intensity metric for the base of the target sequence of the pair, based on the at least one chromatogram-related output; and determining a target-associated abundance ratio (e.g., a ratio of the peak intensity metric for the base of the target sequence to the peak intensity metric for the base of the target-associated molecule sequence; etc.) of the set of target-associated abundance ratios, based on the peak intensity metric for the base of the target-associated sequence and the peak intensity metric for the base of the target sequence; determining an overall target-associated abundance ratio based on the set of target-associated abundance ratios; and/or facilitating the prenatal diagnosis of the genetic disorder based on a comparison between the overall target-associated abundance ratio and a reference-associated overall abundance ratio (and/or other suitable reference-associated abundance metrics; etc.) describing abundance of a biological reference relative reference-associated molecules.

In a specific example, the method 100 (e.g., for facilitating characterization of a medical condition, such as one or more genetic disorders and/or cancer conditions, from a sample including target molecules, etc.) can include: generating a set of target-associated molecules including a target-associated sequence including: a target-associated region with sequence similarity to a target sequence region of a target sequence of a biological target, where the biological target is associated with the genetic disorder; and a target variation region with sequence dissimilarity to a sequence region of the target sequence; performing Sanger sequencing based on the set of target-associated molecules and the target molecules including the target sequence, to determine at least one chromatogram-related output including a set of peaks associated with the target-associated region, the target sequence region of the biological target, the target variation region, and the sequence region of the biological target; determining a set of target-associated abundance ratios (and/or other suitable abundance metrics; etc.) for a set of different pairs of bases based on the set of peaks of the at least one chromatogram-related output, where each different pair of bases, from the set of different pairs of bases, corresponds to a pair of a base of the target-associated sequence and a base of the target sequence; and/or facilitating the characterization (e.g., detection, diagnosis, etc.) of the medical condition based on the set of target-associated abundance ratios and a set of reference-associated abundance ratios (and/or other suitable reference-associated abundance metrics; etc.) describing abundance of a biological reference relative reference-associated molecules (e.g., facilitating the characterization based on a comparison between an overall target-associated abundance ratio and an overall reference-associated abundance ratio; where the overall target-associated abundance ratio can be determined based on combination of the set of target-associated abundance ratios; where the overall reference-associated abundance ratio can be determined based on combination of the set of reference-associated abundance ratios; etc.).

In a specific example, the method 100 (e.g., for biological target quantification from a sample including target molecules, etc.) can include: determining at least one chromatogram-related output associated with a set of target-associated molecules and a set of target molecules, based on Sanger sequencing (e.g., by a third party, by any suitable entity; etc.) associated with the set of target-associated molecules and the set of target molecules, where the set of target-associated molecules includes a target-associated sequence including: a target-associated region with sequence similarity to a target sequence region of a target sequence of a biological target, where the set of target molecules includes the target sequence region; and a target variation region with sequence dissimilarity to a sequence region of the target sequence; determining a set of target-associated abundance ratios (and/or other suitable abundance metrics; etc.) for different sets of bases based on the at least one chromatogram-related output, where each different set of bases, from the different sets of bases, includes at least one base of the target-associated sequence and at least one base of the target sequence; and/or determining an overall abundance metric describing an abundance of the biological target for the sample, based on the set of target-associated abundance ratios.

In a specific example, the method 100 can include: generating a set of target-associated nucleic acids (e.g., spike-in nucleic acids; etc.), where the nucleic acids include one or more target-associated regions (e.g., the set of target-associated nucleic acids including a target-associated nucleic acid sequence including the target-associated region; sequence regions including a nucleotide sequence matching a target sequence region of a target sequence of a target molecule in the sample, where the target molecules correspond to the biological target; etc.) associated with a target chromosome (e.g., chromosome 21; where different sets of target-associated nucleic acids can be generated, where different sets can correspond to different loci of chromosome 21 and can include different target-associated regions with sequence similarity to different target sequence regions of target sequences, where the different target sequence regions or the target sequences can correspond to different loci; etc.), and include one or more variation regions (e.g., sequence insertions; sequence deletions; variation sequences with a plurality of shuffled bases relative a target sequence, such as a target sequence identifying chromosome 21, etc.); combining the set of target-associated nucleic acids with a set of target nucleic acids (e.g., endogenous DNA molecules identifying chromosome 21) from a sample (e.g., a maternal blood sample from a pregnant female; etc.); co-amplifying the set of target-associated nucleic acids and the set of target nucleic acids (e.g., for each different set of target-associated nucleic acids corresponding to a different loci, co-amplifying the set of target-associated nucleic acids with the set of target nucleic acids corresponding to the loci; etc.) based on a set of target-associated primers (e.g., targeting a sequence shared by the target-associated nucleic acids and the target nucleic acids), thereby generating one or more spike-in mixtures; performing Sanger sequencing on the one or more spike-in mixtures (and/or the set of target-associated nucleic acids separately, the target nucleic acids separately, and/or other suitable molecules) to determine one or more chromatogram-related outputs; performing statistical estimation analysis (e.g. general linear regression, non-negative least squares, compressive sensing, random sample consensus; etc.) on the one or more chromatogram-related outputs (e.g., chromatograms from the Sanger sequencing; peak data, such as peak intensity data including peak intensity metrics, from the Sanger sequencing; etc.) for pairs of target sequence base and target-associated sequence base (e.g., for pairs of the same base type corresponding to an original sequence position for the target sequence and a shifted sequence position for the target-associated sequence, such as where the variation region of the target-associated sequence includes one or more insertions and/or deletions; at positions corresponding to the variation region, such as where the variation region includes a set of shuffled base types relative the target sequence; etc.); for each pair, extracting an individual abundance ratio of endogenous to spike-in based on comparing a peak intensity metric (e.g., a maximum intensity for the peak; an overall intensity for the peak; etc.) (and/or other suitable sequencing output) for the target sequence base to a peak intensity metric (and/or other suitable sequencing output) for the target-associated sequence base; generating an overall abundance ratio based on the individual abundance ratios (e.g., averaging individual abundance ratios for different pairs of target sequence base and target-associated sequence base associated with a plurality of target loci for chromosome 21; averaging abundance ratios across loci; etc.); and facilitating one or more characterizations of one or more conditions (e.g., Down syndrome diagnosis, other condition characterizations, analyses of the sequencing outputs, etc.) based on the abundance ratios (e.g., based on comparing the overall abundance ratio for chromosome 21 to a reference overall abundance ratio calculated for a reference chromosome such as chromosome 18 based on processing reference-associated molecules with reference molecules from the sample according to portions of an embodiment of the method 100; where the comparison can facilitating characterization of Down syndrome and Edwards syndrome; etc.).

Embodiments of the method 100 and/or system 200 can function to improve cost-effectiveness (e.g., through leveraging Sanger sequencing technology, etc.), deployability (e.g., in countries with limited access to genome sequencing systems, etc.), and accuracy (e.g., associated with coefficient of variation of less than 1% and/or any suitable accuracy, etc.) in relation to determining abundance metrics (e.g., molecule counts) for one or more biological targets. Embodiments of the method 100 and/or system 200 can additionally or alternatively function to leverage the abundance metrics to characterize (e.g., diagnose) and/or treat (e.g., through treatment determination, treatment evaluation and modification over time, etc.) one or more conditions. Embodiments of the method 100 and/or system 200 can additionally or alternatively function to overcome issues with conventional approaches, such as by increasing multiplexing capacity over applications (e.g., digital PCR), improving accuracy over applications (e.g., qPCR), and/or any other suitable improvements. However, embodiments can include any suitable functionality.

Embodiments of the method 100 and/or system 200 can be used in association with one or more conditions (e.g., in association with characterizing, diagnosing, treating, and/or performing processes related to one or more conditions; etc.), where the conditions can include and/or otherwise be associated with one or more of: noninvasive prenatal testing (NIPT) (e.g., in relation to genetic screening for presence of chromosomal abnormalities including aneuploidy, such as trisomy 21 or Down syndrome, trisomy 18 or Edwards syndrome, trisomy 13 or Patau syndrome, sex chromosome aneuploidies such as Turner syndrome, other suitable aneuploidies; chromosomal abnormalities including DiGeorge syndrome; in relation to genetic screening for single gene disorders; rare variant-associated conditions; etc.); other prenatal testing; aneuploidy analysis and/or other suitable analysis outside of a prenatal context; genetic disorders (e.g., single gene disorders including sickle cell disease and/or rare variant-associated conditions; chromosomal abnormalities; disorders associated with gene amplification; gene deletion; partial chromosomal abnormalities; 22q11.2 deletion syndrome or DiGeorge syndrome; Charcot-Marie-Tooth syndrome, cystic fibrosis, Huntington's disease; Duchenne muscular dystrophy; hemophilia, thalassemia; rare variant-associated conditions etc.), other conditions associated with chromosome abnormalities (e.g., additional, missing, irregular chromosomal DNA, etc.), rare variant-associated conditions, cancer (e.g., through analyzing gene amplifications of oncogenes in tumor biopsies; through analyses associated with one or more of HER2, MET, MYC-N, MYC-C, EGFR, FGFR1, ER/PR, KRAS, UGT1A1, c-KIT, CD20, CD30, FIP1L1-PDGFRalpha, PDGFR, VCR/ABL, PML/RAR-alpha, TPMT, UGT1A1, EML4/ALK, BRAF, and/or any other suitable oncogenes, cancer biomarkers, and/or other cancer-associated targets; analyzing biopsy samples to evaluate the prevalence of circulating-tumor DNA over time in determining and/or evaluating treatments such as herceptin; etc.), and/or any other suitable conditions. Conditions can additionally or alternatively include: psychiatric and behavioral conditions (e.g., a psychological disorder; depression; psychosis; etc.); communication-related conditions (e.g., expressive language disorder; stuttering; phonological disorder; autism disorder; voice conditions; hearing conditions; eye conditions; etc.); sleep-related conditions (e.g., insomnia, sleep apnea; etc.); cardiovascular-related conditions (e.g., coronary artery disease; high blood pressure; etc.); metabolic-related conditions (e.g., diabetes, etc.), rheumatoid-related conditions (e.g., arthritis, etc.); weight-related conditions (e.g., obesity, etc.); pain-related conditions; endocrine-related conditions; genetic-related conditions; chronic disease; and/or any other suitable type of conditions.

Embodiments of the method 100 and/or system 200 can additionally or alternatively transform entities (e.g., samples, targets, references, synthesized molecules, users, sample handling systems, sequencing systems, computational systems, etc.) into different states or things. For example, the method 100 can include synthesizing spike-in molecules (e.g., target-associated molecules, etc.) including shared regions (e.g., a shared nucleotide sequence) and variation regions (e.g., a shuffled nucleotide sequence) relative a biological target, where such spike-in molecules can be processed alongside target molecules (e.g., co-amplified with the target molecules, using the same primers, etc.) for transformation into forms suitable for accurate abundance determination while minimizing amplification bias (e.g., where co-amplification occurs at the same efficiency for both the target-associated molecules and the target molecules; etc.), such as through performing Sanger sequencing and associated computational analysis based on results from the Sanger sequencing with the spike-in mixtures. Such processes can enable previously unperformable abundance quantification (e.g., for target molecules, for reference molecules, etc.), condition characterizations (e.g., improved diagnoses for one or more conditions; etc.), and/or treatment (e.g., through facilitating improved accuracy for meaningful quantification and comparisons of spike-in molecules and target molecules, such as target molecules associated with different loci; through facilitating abundance determination over time for treatment provision and evaluation over time; etc.). However, embodiments of the method 100 and/or system 200 can provide any other suitable benefit(s), such as in the context of using non-generalized components of portions of embodiments of the system 200 for performing unconventional portions of embodiments of the method 100.

Additionally or alternatively, data described herein (e.g., abundance metrics; characterizations; sequencing outputs; ratios; identifiers; molecule designs such as target-associated molecule designs, reference-associated molecule designs, primer designs, experiment designs; sequence designs; sequence region designs; experimental results; validation results; condition-related data; treatment-related data; etc.) can be associated with any suitable temporal indicators (e.g., seconds, minutes, hours, days, weeks, time periods, time points, timestamps, etc.) including one or more: temporal indicators indicating when the data was collected, determined, transmitted, received, and/or otherwise processed; temporal indicators providing context to content described by the data, such as temporal indicators indicating different stages of spike-in mixture generation and/or suitable sequencing library preparation and/or sequencing; changes in temporal indicators (e.g., data over time, such as abundance metrics over time, which can be used in facilitating characterization of one or more conditions and/or facilitating treatment, such as in relation to cancer condition monitoring; change in data; data patterns; data trends; data extrapolation and/or other prediction; etc.); and/or any other suitable indicators related to time.

Additionally or alternatively, parameters, metrics, inputs, outputs, and/or other suitable data described herein can be associated with value types including any one or more of: scores, binary values, classifications, confidence levels, identifiers (e.g., sample identifiers, molecule identifiers for any suitable molecules described herein, etc.), values along a spectrum, and/or any other suitable types of values. Any suitable types of data described herein can be used as inputs, generated as outputs, and/or manipulated in any suitable manner for any suitable components associated with embodiments of the method 100 and/or system 200.

One or more instances and/or portions of embodiments of the method 100 and/or processes described herein can be performed asynchronously (e.g., sequentially), concurrently (e.g., in parallel; concurrently processing samples in a multiplex, automated manner; concurrently computationally processing Sanger sequencing-produced outputs such as peak data and/or chromatograms to improve system processing ability; any suitable concurrent computational processing for any suitable number of samples, mixtures, sequencing outputs, and/or other components; multiplex sample preparation and/or sequencing operations; etc.), in temporal relation to a trigger event, and/or in any other suitable order at any suitable time and frequency by and/or using one or more instances of the system 200, components, and/or entities described herein.

Embodiments of the system 200 can include one or more sample handling networks configured to generate molecules (e.g., target-associated molecules; reference-associated molecules; etc.), process samples (e.g., biological samples; synthetic samples; samples from users; etc.), and/or perform other suitable processes; one or more sequencing systems (e.g., Sanger sequencing systems; etc.) configured to sequence processed genetic material from spike-in mixtures, other mixtures, and suitable samples, and/or any suitable components; one or more computing systems (e.g., remote computing system, local computing system, etc.) configured to analyze sequencing outputs of the one or more sequencing systems (e.g., in determining one or more abundance metrics; in facilitating characterizations of one or more conditions; in facilitating treatment; etc.); and/or any other suitable components. Portions of embodiments of the method 100 and/or system 200 are preferably performed by a first part but can additionally or alternatively be performed by one or more third parties, users, and/or any suitable entities (e.g., care providers, lab technicians, etc.).

However, the method 100 and system 200 can be configured in any suitable manner.

2.1 Generating Target-Associated Molecules.

Embodiments of the method 100 can include generating one or more target-associated molecules S110 (e.g., associated with one or more biological targets, etc.), which can function to synthesize one or more molecules sharing one or more characteristics (e.g., sequence characteristics, functional characteristics, structural characteristics, evolutionary characteristics, etc.) with the one or more targets (e.g., biological targets; etc.), which can facilitate similar sample processing parameters (e.g., Sanger sequencing conditions for sequencing of a spike-in mixture including the target-associated molecules and the target molecules, for sequencing the target-associated molecules individually or the target molecules individually; similar amplification parameters during PCR-based amplification, such as through co-amplification of target-associated molecules and target molecules, of reference-associated molecules and reference molecules; etc.) to reduce bias (e.g., amplification bias, etc.) and/or to improve accuracy during downstream processing (e.g., for statistical estimation such as linear regression; peak analysis; association and/or identification of pairs and/or sets of bases of different sequence for facilitating abundance ratio determination; deconvolution; performance of multiple instances of embodiments of the method 100 over time; etc.).

Target-associated molecules preferably include one or more target-associated sequences (e.g., nucleotide sequences; each target-associated molecule of a set of target-associated molecules corresponding to a same or similar target-associated molecule sequence; etc.), where a target-associated sequence can include one or more target-associated regions. For example, a target-associated sequence can include a target-associated region with sequence similarity (e.g., full sequence similarity; sequence similarity greater than a threshold percentage and/or amount; etc.) to one or more target sequence regions of one or more target sequences of one or more biological targets (e.g., a target sequence corresponding to the biological target; etc.), where the one or more biological targets can be associated with one or more medical conditions.

Figure 3:
FIG. 3 includes specific examples of a target sequence, a target-associated sequence, and associated primers (hg19=SEQ ID NO: 1: spk=SEQ ID NO: 2: chr21:14439004 PCR2 FP=SEQ ID NO: 3: chr21:14439076 PCR2 RP hp=SEQ ID NO: 4: chr21:14439004 PCR1 FP=SEQ ID NO: 5: chr21:14439076 PCR1 RP=SEQ ID NO: 6)

Target-associated regions (and/or the target-associated molecules and/or target-associated sequences) are preferably associated with (e.g., sharing nucleotide sequences with; sharing sets of bases with a target sequence at corresponding positions; able to be processed with; able to be Sanger sequenced with; able to be amplified with, such as through co-amplification; able to be targeted by the same primers; complementary to; targeting; digitally associated with in a computing system; etc.) one or more biological targets and/or target molecules (e.g., target molecules corresponding to biological targets; target molecules including target sequence regions of biological targets; etc.). Biological targets (e.g., target markers; corresponding to, causing, contributing to, therapeutic in relation to, correlated with, and/or otherwise associated with one or more medical conditions; targets of interest; known or identified targets; unknown or previously unidentified targets; etc.) can include any one or more of target sequence regions (e.g., sequences identifying a chromosome; sequences indicative of a condition; sequences that are invariant across a population and/or any suitable set of subjects; conserved sequences; sequences including mutations, polymorphisms; nucleotide sequences; amino acid sequences; etc.), genes (e.g., associated with one or more single gene disorders, etc.), loci, chromosomes (e.g., associated with one or more chromosomal abnormalities; etc.) proteins (e.g., serum proteins, antibodies, etc.), peptides, carbohydrates, lipids, nucleic acids (e.g., extracellular RNA, microRNA, messenger RNA, where abundance determination for RNA targets can include suitable reverse transcriptase operations, etc.), cells (e.g., whole cells, etc.), metabolites, natural products, cancer biomarkers (e.g., molecules secreted by tumors; molecules secreted in response to presence of cancer; etc.), genetic predisposition biomarkers, diagnostic biomarkers, prognostic biomarkers, predictive biomarkers, other molecular biomarkers, gene expression markers, imaging biomarkers, and/or other suitable targets. Targets are preferably associated with conditions described herein, and can additionally or alternatively be associated with one or more conditions including: symptoms, causes, diseases, disorders, and/or any other suitable aspects associated with conditions. In an example, target-associated molecules can include nucleotide sequences identical to one or more regions of a target sequence of a target molecule (e.g., identifying chromosome 21), where primers can concurrently target both the target-associated molecules and the target molecules by targeting the identical regions (e.g., for facilitating co-amplification, such as to reduce amplification bias, etc.). In an example, as shown in FIG. 3, a target-associated sequence (e.g., "spk" sequence), can include target-associated regions with sequence similarity to target sequence regions of the target sequence (e.g., "hg19" sequence), such as where a set of primers (e.g., for a first PCR process, for a second PCR process; "chr21:14439004_PCR2_FP", "chr21:14439076_PCR2_RP_hp", "chr21:14439004_PCR1_FP", "chr21:14439076_PCR1_RP"; PCR primers including one or more hairpin sequences; etc.) can target both the target-associated sequence and the target sequence (e.g., for facilitating co-amplification and corresponding reduction of amplification biases; etc.). In an example, target-associated molecules can include sequences with any suitable sequence identity to target sequences, where any number and/or type of primers can be used in concurrently or separately targeting the target-associated molecules and target molecules. In a specific example, the biological targets can include target sequences identifying a chromosome corresponding to an aneuploidy-associated condition (e.g., in relation to NIPT for aneuploidies in chromosomes 21, 18, 13, etc.). In a specific example, the biological targets can include target sequences identifying oncogenes (e.g., in relation to determining cancer condition metrics, evaluating cancer treatments, etc.). However, targets (e.g., biological targets, etc.) can be configured in any suitable manner. Additionally or alternatively, target-associated molecules (e.g., target-associated regions of target-associated molecules; etc.) can share any suitable characteristics (e.g., components, etc.) with biological targets (e.g., with target molecules corresponding to biological targets; etc.), such as to facilitate similar sample processing parameters to be able to subsequently generate meaningful comparisons between abundance metrics for the target-associated molecules and the target molecules. However, target-associated molecules can be configured in any suitable manner.

As shown in FIG. 11, target-associated molecules preferably include target variation regions (e.g., variation regions of target-associated sequences of target-associated molecules; each target-associated molecule including one or more variation regions; etc.), where a variation region can include different characteristics from the characteristics of the target molecule. Variation regions preferably include one or more variations (e.g., insertions, deletions, substitutions, etc.), such as variations that can enable a corresponding target-associated molecule (e.g., the target-associated molecule including a target-associated sequence including the variation region; etc.) to proceed through sample processing operations in a similar manner to the corresponding target molecules (e.g., nucleic acids including a target sequence region of a biological target; etc.), while facilitating differentiation of the target-associated molecules from the target molecules (e.g., during determining of sequencing outputs; during determination of abundance metrics, such as performing statistical estimation analysis; for facilitating characterizations and/or treatments of one or more medical conditions; during post-processing of chromatogram-related outputs from Sanger sequencing of spike-in mixtures and/or suitable samples; such as during deconvolution of overlapping peaks for pairs of target-associated base and target base, such as pairs corresponding to positions of variation regions and/or other suitable regions; during statistical estimation analyses to fit the abundances for target-associated sequences and target sequences; etc.). Such differentiation can facilitate determination of different corresponding abundance metrics that can be meaningful compared (e.g., quantitative comparison between peak intensities of pairs and/or sets of bases; comparison and/or combination of individual abundance metrics, such as to determine overall abundance metrics; such as for facilitating characterization and/or treatment; etc.) In an example, the variation region can include a sequence variation region including a nucleotide sequence differing from a sequence region of a target sequence of a target molecule. In a specific example, as shown in FIG. 3, a target-associated sequence (e.g., "spk" sequence; etc.), can include a deletion (e.g., a three nucleotide deletion; etc.) relative a sequence region of the target sequence (e.g., relative an "att" sequence region of the "hg19" target sequence; etc.). Additionally or alternatively, variation regions can include any suitable number of substitutions, insertions, deletions, and/or other modifications of any suitable size (e.g., insertions and/or deletions of any suitable number of nucleotides; any suitable number of point mutations, such as 10 point mutations; etc.) in relation to any suitable bases and/or base types.

In a specific example, the variation regions can facilitate determination of sequencing outputs (e.g., peak intensities, peak area, peak data, chromatograms, etc.) for any target-associated base (e.g., of a target-associated sequence; etc.) and/or target base (e.g., of a target sequence; etc.), such as where a sequencing output (e.g., peak intensity metric) for a target-associated base at one or more regions (e.g., a target-associated region, a variation region, etc.) can be compared to a sequencing output (e.g., peak intensity metric, etc.) for a corresponding target base at a different position (e.g., where a position of a corresponding base can be shifted due to one or more insertions and/or deletions of a variation region; etc.) or same position (e.g., for point substitutions of a variation region; etc.), such as for determining one or more abundance metrics. In a specific example, as shown in FIG. 11, the target-associated molecule can include a nucleotide sequence variation region differing from the corresponding target nucleotide sequence by 10 bases (e.g., where the target sequence includes a "TCTTGGATAG" region (portion of SEQ ID NO: 11) and where the variation region includes a "CTGGTTTAGA" region (portion of SEQ ID NO: 12) at corresponding positions, etc.), where each of the 10 base difference can enable a different individual abundance ratio metric of endogenous to spike-in that can be used in generating an overall abundance ratio of improved accuracy. Additionally or alternatively, the variation region can include differences (e.g., relative a target sequence, etc.) of any suitable number of bases.

Variation regions can be designed in coordination with the target-associated regions to facilitate appropriate sequence dissimilarity and sequence similarity, respectively (e.g., determining characteristics of the variation regions and/or target-associated regions to facilitate improved sequencing outputs given sequencing parameters associated with the sequencing technologies, such as Sanger sequencing; etc.).

Sequence variation regions can differ by target sequences by any suitable number and type of bases, at any suitable positions (e.g., sequential positions, non-sequential; etc.), across any suitable loci, for any suitable chromosome and/or other target, and/or can differ from target sequences in any suitable manner. Sequence variation regions can include any one or more of substitutions, insertions, deletions, any suitable mutation types, and/or any suitable modifications (e.g., relative one or more sequence regions of a target sequence and/or biological target; etc.).

In a variation, sequence variation regions can include randomly shuffled bases (e.g., in equal proportion of base types, in predetermined portions for the base types, etc.). In a variation, the method 100 can include selecting bases of the target sequence to modify (e.g., based on optimizing Sanger sequencing output results, such as through selecting a specific sequence of base types to account for a Sanger output quality dependence on order of bases and base type in a sequence; based on facilitating statistical estimation, unmixing, deconvolution during computational post-processing; based on a number of base differences required to achieve a threshold abundance metric accuracy while minimizing amplification biases; etc.).

Additionally or alternatively, variation regions can include non-sequence variation regions, with functional, structural, evolutionary, and/or other suitable characteristics that are different from the characteristics of the one or more target molecules (e.g., of any suitable type, etc.). However, variation regions can be configured in any suitable manner, and target-associated molecules can include any suitable nucleotide sequence regions.

In variations, target-associated molecules can include one or more sequencing regions (e.g., of sequencing molecules; etc.) configured to aid in sequencing operations (e.g., operation of sequencing systems; determination of sequencing outputs, such as of increased accuracy and/or of a form enabling quantitative comparison and/or quantification; etc.) S130, determining abundance metrics S140, and/or any suitable portions of the method 100 (e.g., facilitating characterizations S150 and/or facilitating treatment S16; etc.). In a variation, a target-associated molecule (e.g., a target-associated sequence of a target-associated molecule; etc.) can include (e.g., through addition of, etc.) one or more Sanger-associated sequence regions (e.g., configured to improve Sanger sequencing outputs, etc.) and/or any suitable sequencing regions, which can include any one or more of additional target-associated regions (e.g., with sequence similarity to additional target sequence regions of one or more target sequences, such as the same or different target sequences, of one or more biological targets, such as the same or different biological targets; etc.); sequence repeats (e.g., of any suitable regions of target-associated molecules, target molecules, reference-associated molecules, reference molecules, any suitable sequences, regions, and/or molecules described herein; etc.); and/or any suitable sequence regions (e.g., sequencing regions described herein in relation to being added to one or more molecules; etc.).

Figure 13A:
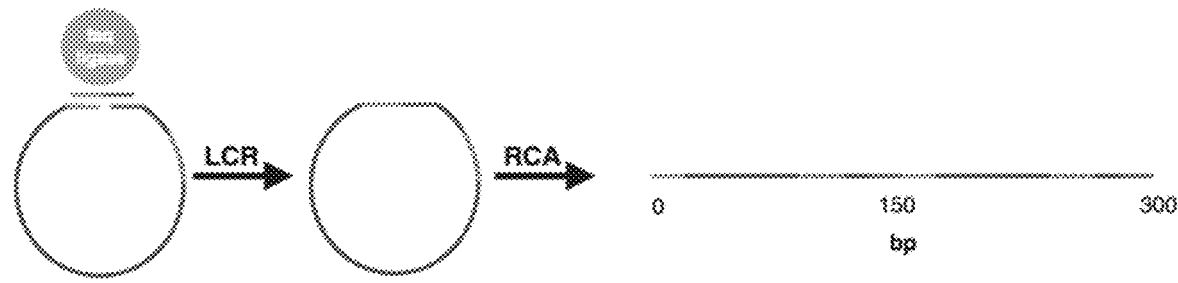
FIGS. 13A-13B include a schematic representation of portions of a variation of an embodiment of a method (Chr21:30934064=SEO ID NO: 13, Chr18:216603=SEO ID NO: 14; Chr21:47856292=SEQ ID NO: 15).
Figure 13B:
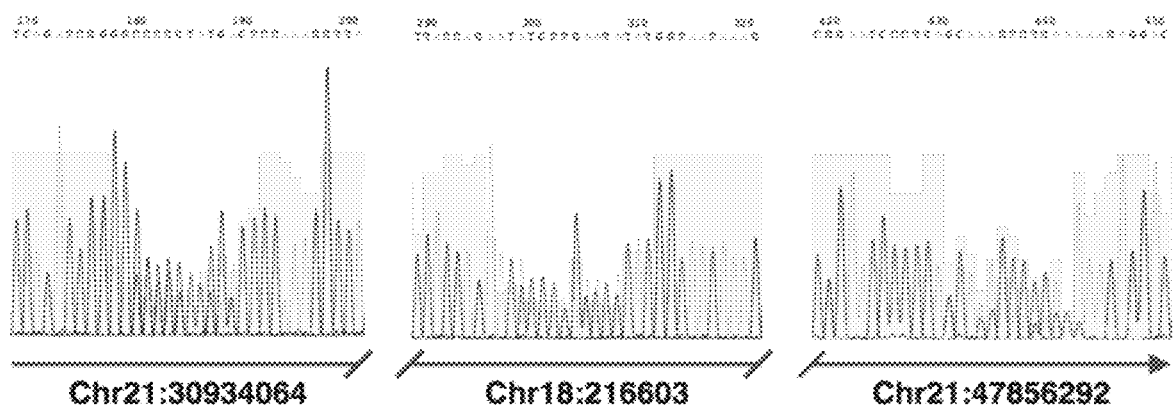

In a variation, the Sanger-associated sequence regions can include specific nucleotide sequences (e.g., of a predetermined length, with specifically selected nucleotides; etc.) preceding (and/or in any suitable positional relationship with) a sequence variation region and/or other suitable region of the target-associated molecule, which can facilitate repositioning of the sequence variation region to be at positions (e.g., at bases 100-500, at bases 200-500, during Sanger sequencing, and/or at any suitable positions) corresponding to improved Sanger sequencing chromatogram-related outputs. In a specific example, Sanger BigDye 1.1 chemistry can be applied for improved accuracy in relation to the beginning regions of a sequence (e.g., where LCR and/or RCA, such as shown in FIGS. 13A-13B, can be omitted; etc.). In a specific example, Sanger BigDye 3.1 chemistry can be applied to enable longer sequencing reads, where a beginning sequence region (e.g., around 200 bp and/or other suitable size) can be used (e.g., inserted prior to the target sequence region and/or target-associated sequence region) for improved accuracy (e.g., such as through LCR and/or RCA, such as shown in FIGS. 13A-13B, which can enable multiplexing). However, Sanger-associated sequence regions can be configured in any suitable manner.

Additionally or alternatively, sequencing molecules can include sequencing primers configured to facilitate processes by sequencing systems, adapter sequences, and/or other suitable components associated with any suitable sequencing systems. However, sequencing molecules can be configured in any suitable manner.

The target-associated molecules (and/or other suitable components described herein, such as reference-associated molecules, components of spike-in mixtures, etc.) can be of any suitable size (e.g., 100-500 base pairs, 200-500 base pairs, in length and including repeats of sequence regions, such as target-associated regions and/or variation regions; similar or different length as target molecules; 80-150 base pairs in length, including a variation region of 10 base pairs of shuffled base types; etc.). The set of target-associated molecules can include any number of target-associated molecules associated with any suitable number of targets (e.g., any number of target sequences associated with any number of loci, chromosomes, cancer biomarkers, target biomarkers, etc.), samples (e.g., concurrently synthesizing a batch of molecules for use with samples across multiple users, for user with multiple samples for a single user, to improve efficiency of the sample handling system; etc.), conditions (e.g., set of target-associated molecules associated with biological targets associated with different conditions; etc.), and/or other suitable aspects.

In variations, generating target-associated molecules can include generating different types of target-associated molecules (e.g., including different target-associated regions, different variation regions, different sequence molecules, etc.), such as sets of target-associated molecules (e.g., each set corresponding to a different type of target-associated molecules; etc.). Target-associated molecules can include sets of target-associated molecules (e.g., a plurality of different sets, etc.), each set including a different target-associated region associated with (e.g., with sequence similarity to; etc.) a different target sequence region (e.g., different target sequence regions of a same target sequence and/or biological target such as a chromosome; different target sequence regions of different target sequences and/or biological targets such as different genes; etc.), which can facilitate different pairs and/or sets of a target-associated region type (e.g., corresponding to a specific target-associated region sequence; etc.) and a target sequence region type (e.g., corresponding to a specific target sequence of a biological target; etc.), and/or different pair and/or sets of bases (e.g., where the bases of the pair and/or set can be from a target-associated sequence and a target sequence; etc.), such as to determine corresponding abundance metrics such as individual abundance ratios (e.g., corresponding to the different pairs; such as individual abundance ratios corresponding to different sets of bases, where the different sets of bases can correspond to different loci of a chromosome biological target; etc.), which can be used in determining an overall abundance metric with increased accuracy through, for example, averaging and/or performing any suitable combination operations with the individual abundance metrics.

Figure 9:
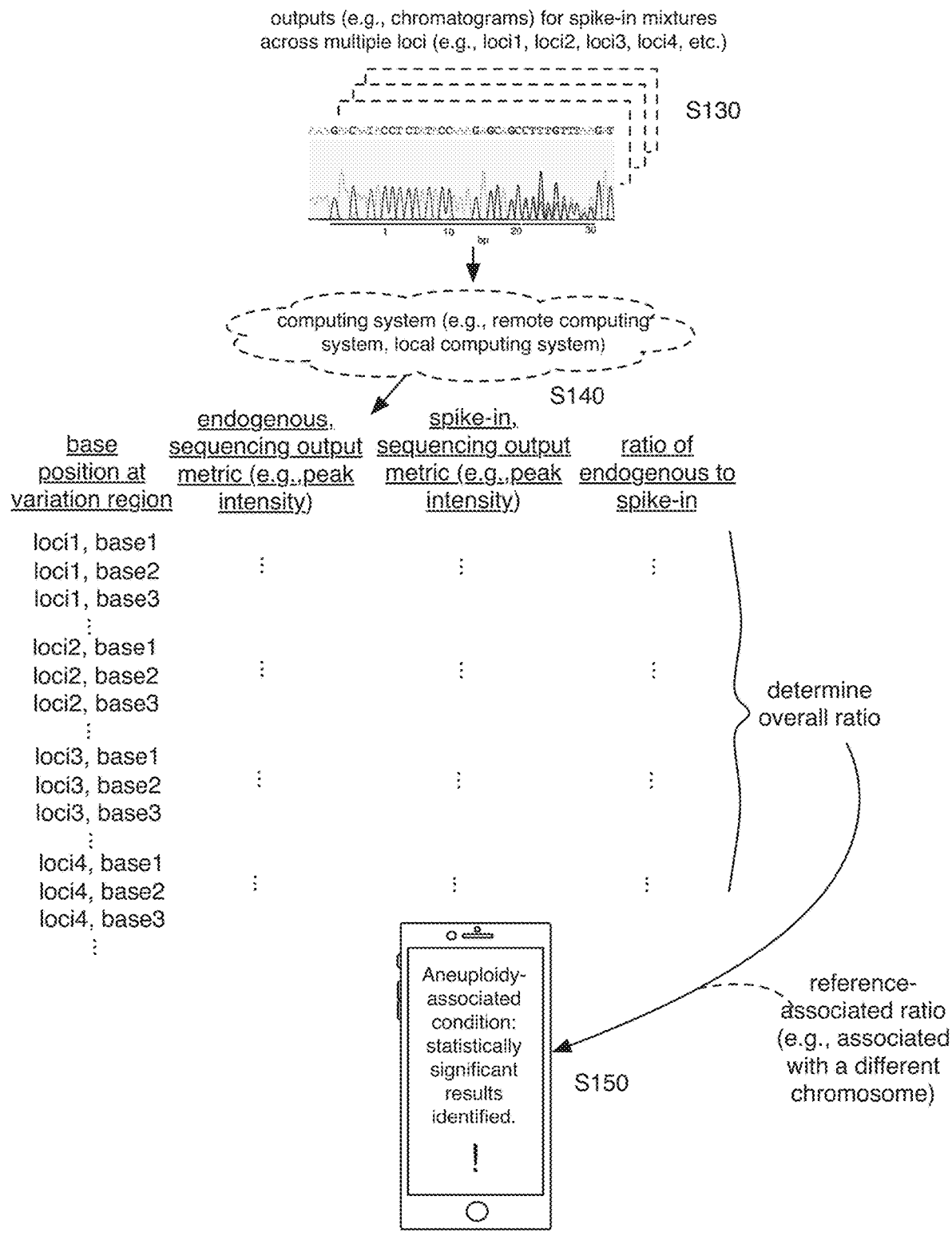
FIG. 9 includes a schematic representation of a variation of an embodiment of a method (specific example of outputs (e.g., chromatograms) for spike-in mixtures across multiple loci (e.g., loci1, loci2, loci3, loci4, etc.)=SEQ ID NO: 10.

In a specific example, different sets of target-associated molecules can be associated with different target sequences (and/or target sequence regions, etc.) across different loci. In a specific example, each set can be associated with a different locus for the same chromosome (e.g., a first, second, third, and fourth locus for a chromosome, such as shown in FIG. 9; etc.), where a sequence of a target-associated molecule of a given set can include a sequence region shared by the locus corresponding to the set, and can include a sequence variation region differing (e.g., by insertions, deletions, base substitutions, etc.) from the sequence for the locus.

Any number of sets of target-associated molecules and/or any number of types of target-associated molecules can be generated and/or associated with any suitable number of biological targets. In an example, selecting different target-associated molecule sets can be based on sequencing parameters, accuracy requirements for a given condition and/or application (e.g., selecting a number of sets leading to a corresponding suitable number of individual abundance metrics to be used in achieving a target accuracy for diagnosing Down syndrome), and/or can be selected based on any suitable criteria (e.g., parameter to be optimized). However, generating different sets of target-associated molecules can be performed in any suitable manner.

Generating target-associated molecules can include determining target sequences (e.g., target sequence regions of target sequences; any suitable regions of target sequences; etc.), which can function to select target sequences upon which the generation of target-associated molecules can be based. Determining target sequences can be based on any one or more of: condition (e.g., selecting target sequences identifying chromosome 21 for facilitating Down syndrome diagnosis; selecting target sequences identifying oncogenes; etc.), sequencing parameters (e.g., selecting target sequences of a particular length, nucleotide sequence, and/or other parameter for optimizing chromatogram-related output quality from Sanger sequencing; for generating chromatogram-related outputs suitable for statistical estimation analysis and/or other suitable; for reducing cost, improving accuracy, improving reproducibility, and/or for other suitable optimizations in relation to sequencing systems and/or operations, etc.); amplification parameters (e.g., selecting target sequences of a particular length, nucleotide sequence, and/or other parameter for optimizing amplification specificity, such as in relation to primer specificity for the target sequences in relation to polymerase chain reaction amplification; etc.), other sample processing parameters, and/or other suitable criteria. In an example, determining target sequences can include computationally searching a database (e.g., DNA database, genome database, gene expression database, phenotype database, RNA database, protein databases, etc.) to generate a target sequence candidate list; and filtering the target sequence candidate list based on criteria described herein, and/or any suitable criteria. In a specific example, determining targeting sequences can include extracting a target sequence candidate list (e.g., based on exome pull down; merge into chunks of a suitable number of base pairs; etc.); filtering out candidates including defined types of mutations and/or polymorphisms (e.g., filtering out candidates associated with common single nucleotide polymorphisms to obtain candidates with relative invariance across subjects of a population, etc.); identifying primers for the remaining candidates (e.g., with a Primer-BLAST for 80-150 bp amplicons); and determining candidate regions that are suitable for variation in generating a variation region of target-associated molecule (e.g., through scrambling bases at positions relative a forward primer and/or other region of the sequence, etc.). However, determining target sequences can be performed in any suitable manner.

Generating the target-associated molecules can include synthesizing the molecules through performing any one or more of: amplification (e.g., PCR amplification, such as with PCR primers including one or more hairpin sequences; etc.), plasmid-based nucleic acid synthesis (e.g., including both target-associated molecules and reference-associated molecules respectively corresponding to different loci of a target chromosome and a reference chromosome; using plasmids including any suitable cut sites, origin of replication sites, multiple cloning sites, selectable markers, reporter markers, backbone, and/or other components; etc.), other artificial gene synthesis techniques, amplification techniques (e.g., polymerase chain reaction, rolling circle amplification, etc.), ligation techniques (e.g., Ligase Cycling Reaction, etc.), phosphoramidite approaches, post-synthetic processing, purification (e.g., using high-performance liquid chromatography or other chromatography approaches, desalting, washing, centrifuging, etc.), tagging techniques (e.g., molecular tagging techniques, fluorescent tagging techniques, particle labeling techniques, etc.), molecule cloning techniques, and/or any suitable sample processing technique.

In a variation, synthesizing target-associated molecules can include generating a target-associated sequence including a plurality of sequence regions associated with different targets (e.g., different loci across the same chromosome, different loci of different chromosomes, different oncogenes, etc.). In a specific example, a type of target-associated molecule can be configured to reduce the number of required sequencing operations (e.g., a target-associated molecule type that facilitates generation of a chromatogram-related output informative of a plurality of targets and generated using a single Sanger sequencing run; etc.); however, target-associated molecule types can be synthesized to optimize for any suitable parameter. Additionally or alternatively, any suitable number of molecules and/or types of molecules associated with any number of targets can be generated at any suitable time and frequency.

However, generating target-associated molecules S110 can be performed in any suitable manner.

2.2 Generating a Spike-In Mixture.

Embodiments of the method 100 can include generating (e.g., facilitating generation of, etc.) one or more spike-in mixtures S120 (e.g., based on processing the set of target-associated molecules with target molecules from one or more samples from a user, etc.), which can function to amplify (e.g., under similar amplification parameters), perform pre-processing upon (e.g., sample preparation, lysis, bead-based processes, other purification and/or nucleic acid extraction techniques, etc.), modify (e.g., generate sequence repeats, combine sequences associated with different targets, etc.) and/or otherwise process the target-associated molecules, target molecules, and/or other suitable molecules (e.g., reference-associated molecules, reference molecules, etc.) into a form suitable for subsequent analysis (e.g., Sanger sequencing, etc.) and abundance metric determination (e.g., based on outputs from the Sanger sequencing, etc.). Collected samples (e.g., biological samples; collected using sample containers provided to users in sample collection kits) can include any one or more of: blood, plasma, serum, tissue, biopsies (e.g., tumor biopsies, etc.), sweat, urine, feces, semen, vaginal discharges, tears, interstitial fluid, other body fluid, and/or any other suitable samples (e.g., associated with a human user, animal, object such as food, microorganisms, etc.). In examples, such as for NIPT, biological samples can include one or more maternal samples. Samples preferably include target molecules (e.g., nucleic acid molecules including one or more target sequences and/or target sequence regions; etc.) and/or reference molecules (e.g., nucleic acid molecules including one or more reference sequences and/or reference sequence regions; etc.), such as where the target molecules can be amplified with the target-associated molecules under similar parameters; where the reference molecules can be amplified with the reference-associated molecules under similar parameters; etc.). Additionally or alternatively, samples can include components (e.g., target molecules) from multiple users (e.g., a blood sample including nucleic acids from a mother and nucleic acids from the mother's unborn baby, where the nucleic acid mixture can be indicative of an abnormal abundance of chromosome 21, etc.), components collected across multiple time periods, and/or components varying across any suitable condition, such that generating spike-in mixture(s) can be performed for any suitable number and type of entities.

Generating one or more spike-in mixtures preferably includes combining target-associated molecules with target molecules (e.g., nucleic acids including target sequence regions and/or target sequences, etc.) from the sample; and/or combining reference-associated molecules with reference molecules; and/or combing any suitable molecules. Combining can include one or more of: combining each of the molecules into a single mixture (e.g., including different subsets of target-associated molecules and corresponding subsets of target molecules; etc.); subsampling the sample (e.g., a preprocessed sample) into a plurality of mixtures, each designated for a different subset of target-associated molecules (e.g., corresponding to different target loci for a target chromosome, etc.); subsampling the sample into different mixtures for target-associated molecules and reference-associated molecules; and/or any other suitable approach to combining the molecules. In an example, target molecules and target-associated molecules (e.g., different pairs of types of target molecules and target-associated molecules; corresponding to different pairs of target-associated regions and target sequence regions; associated with a plurality of different targets; etc.) can be amplified in the same compartment (e.g., tube; etc.) (and/or any suitable number of compartments), such as through multiplex PCR and/or suitable amplification processes, which can facilitate conserving a precious sample; and the resulting amplification products can be subsequently subsampled into separate mixtures for subsequent individual Sanger sequencing targeting different target types (e.g., using a Sanger sequencing primer associated with an invariant region, such as a region of sequence similarity, shared by the target-associated region and target sequence region; etc.). In examples, subsampling and/or other sample modification operations can be performed in any suitable order.

Additionally or alternatively, separate samples (e.g., mixtures, solutions, etc.) can be generated for different types of molecule (e.g., without combining different types of molecules). For example, a first sample including target-associated molecules (e.g., without target molecules) can be generated, and a sample mixture including target molecules (e.g., without target-associated molecules) can be generated, where the first and second mixtures can be separately used in downstream processing (e.g., performing separate Sanger sequencing runs to generate separate chromatogram-related outputs such as separate chromatograms that can be used during statistical estimation, deconvolution, and/or other computational processing operations, such as for determining abundance metrics, etc.). However, any suitable number of samples including any suitable separate or combination of types of molecules can be generated and/or processed.

Combining molecules preferably includes using a known abundance of target-associated molecules, but an unknown abundance of target molecules can alternatively be used (e.g., where results from preceding sequencing runs with the unknown abundance can be used to inform results from subsequent sequencing runs, etc.). Further, combining molecules preferably includes using the same or substantially similar abundances across different subsets of target-associated molecules (e.g., associated with different loci), and/or same or similar abundances relative to reference-associated molecules. Additionally or alternatively, any suitable abundances for different molecule types can be used.

In a variation, combining molecules can include modifying (e.g., during pre-processing) abundances of the target-associated molecules, the reference-associated molecules, and/or other suitable components. For example, modifying abundances of molecules can include measuring initial abundances of the molecules (e.g., abundance of the target-associated molecules); and modifying the abundances (e.g., through dilution, amplification, etc.) based on expected abundances of target molecules (e.g., expected count for endogenous target molecules in the sample, etc.). In a variation, generating spike-in mixtures can omit modification (e.g., during pre-processing) of abundances (e.g., where the abundance results for a first instance of an embodiment of the method 100 can be used in determining a correction factor to be used in subsequent instances of the embodiment of the method 100; etc.). However, combining molecules can be performed in any suitable manner.

Generating the spike-in mixture preferably includes amplifying the target-associated molecules with the target molecules. Amplification can include performing any one or more of: polymerase chain reaction-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction, ligase cycling reaction (LCR), and/or any other suitable amplification techniques and/or associated protocols (e.g., protocols for minimizing amplification bottlenecking). In an example, as shown in FIG. 3, generating a spike-in mixture can include performing a plurality of PCR rounds (e.g., any number of PCR rounds) to co-amplify the target-associated molecules with the target molecules (e.g., using sets of primers targeting a sequence shared by both the target-associated molecules and the target molecules; using different sets of primers corresponding to different primer types and sequences, as shown in FIG. 3, where one or more of the sets of primers can include one or more hairpin sequences, such as for facilitating addition of sequence repeats; etc.).

In a variation, generating a spike-in mixture and/or suitable portions of embodiments of the method 100 (e.g., in variations where samples including target-associated molecules are independently prepared and sequenced from samples including target molecules; in variations where samples including reference-associated molecules are independently prepared and sequenced from samples including reference molecules; etc.) can include adding one or more sequence regions to one or more molecules (e.g., one or more regions and/or sequences of one or more molecules; to target-associated molecules, to target molecules, to reference-associated molecules, to reference molecules, etc.).

Adding sequence regions can include one or more of: generating sequence repeats (e.g., generating a modified sequence including repeats of a target-associated sequence and/or target sequence; etc.); adding sequence regions identifying different targets (e.g., different loci of a chromosome identified by the original target; loci of different chromosomes; sequence regions associated with different conditions; etc.); and/or adding any suitable nucleotide sequences. For example, the method 100 can include adding at least one sequence region to at least one of the set of target-associated molecules and the target molecules, where the at least one sequence region includes at least one of (a) a second target-associated region with sequence similarity to a second target sequence region (e.g., where the set of target-molecules includes a first target-associated region with sequence similarity to a first target sequence region of a target sequence of a biological target; etc.), and (b) at least one sequence repeat of at least one of a region of the target-associated sequence and a region of the target sequence.

Adding sequence regions can function to: facilitate improved output quality from sequencing systems (e.g., quality of chromatogram results), such as through adding sequence regions positionally preceding variation regions upon which abundance metric extraction will be based (e.g., where the added sequence regions can enable repositioning of the variation regions to be at positions corresponding to improved sequencing outputs; etc.); facilitate determination of additional individual abundance metrics for the added sequence regions (e.g., by analyzing sequence repeats of the variation region in relation to corresponding target bases; etc.), which can be used in calculating an overall abundance metric of improved accuracy; facilitate reduction in number and/or cost of required sequencing operations (e.g., fewer Sanger sequencing runs; etc.) to analyze a plurality of targets (e.g., across different loci, chromosomes, etc.), such as through ligating different sequences associated with the different targets.

In an example, the method 100 can include adding at least one sequence repeat (e.g., for facilitating multiple-pass sequencing, such as sequencing sequences a plurality of times, such as in the same or different sequencing runs, such as for increasing sequencing output data, such that the sequencing output data and/or or associated abundance metrics can be averaged and/or otherwise combined, such as to reduce noise; etc.) to one or more target-associated molecules (e.g., one or more regions of a target-associated sequence of the target-associated molecules; etc.) and/or one or more target molecules (e.g., one or more regions of a target sequence of the target molecules; etc.), such as where the first set of peaks of the at least one chromatogram-related output (e.g., chromatogram, peak intensities, other peak data, etc.) correspond to a first sequencing (e.g., from a Sanger sequencing operation; etc.) for the target-associated region, the target sequence region of the biological target, the target variation region, and the sequence region of the biological target, where the at least one chromatogram-related output includes a second set of peaks corresponding to a second sequencing (e.g., from the same Sanger sequencing operation, etc.) for the target-associated region, the target sequence region of the biological target, the target variation region, and the sequence region of the biological target, and where determining a set of target-associated abundance ratios can be based on the first set of peaks and the second set of peaks (e.g., based on individual abundance ratios of peak intensities, from the first and the second set of peaks, for pairs of bases of the target sequence and the target-associated sequence; etc.).

Figure 4:
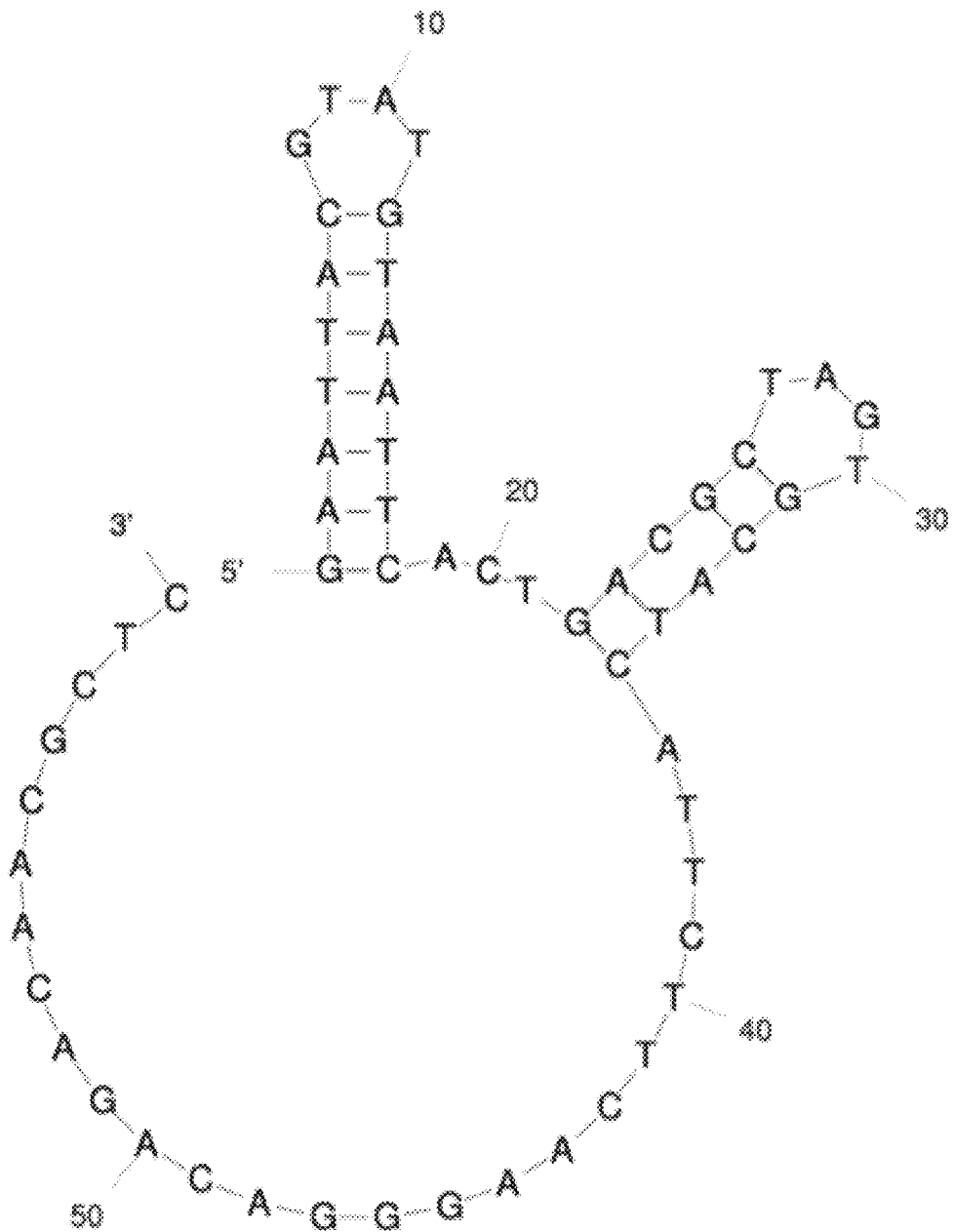
FIG. 4 includes a specific example of a PCR primer including a hairpin sequence (chr21:14439076 PCR2 RP hp=SEQ ID NO: 4)
Figure 5A:
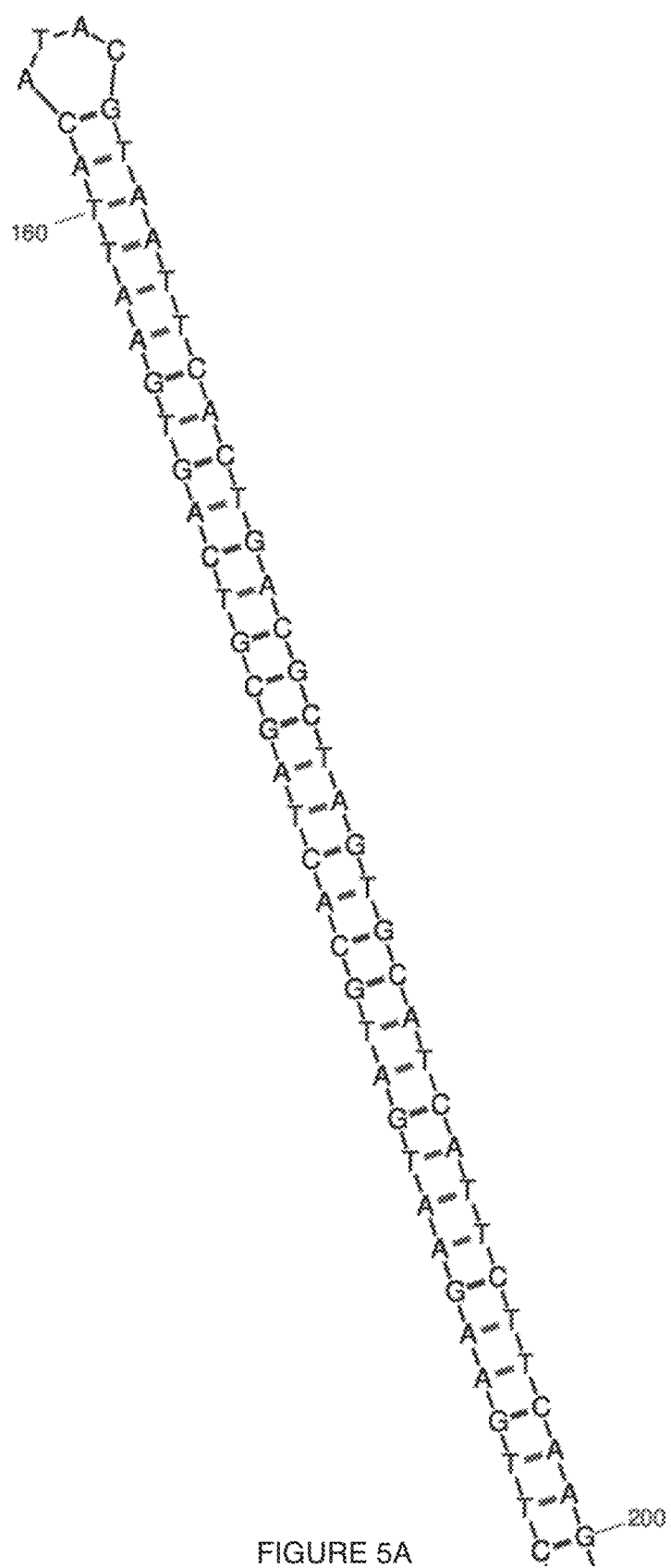
FIGS. 5A-5E (SEQ ID NO: 7) include a specific example of a product from amplification with a PCR primer including a hairpin sequence, in a variation of an embodiment of the method.
Figure 5B:
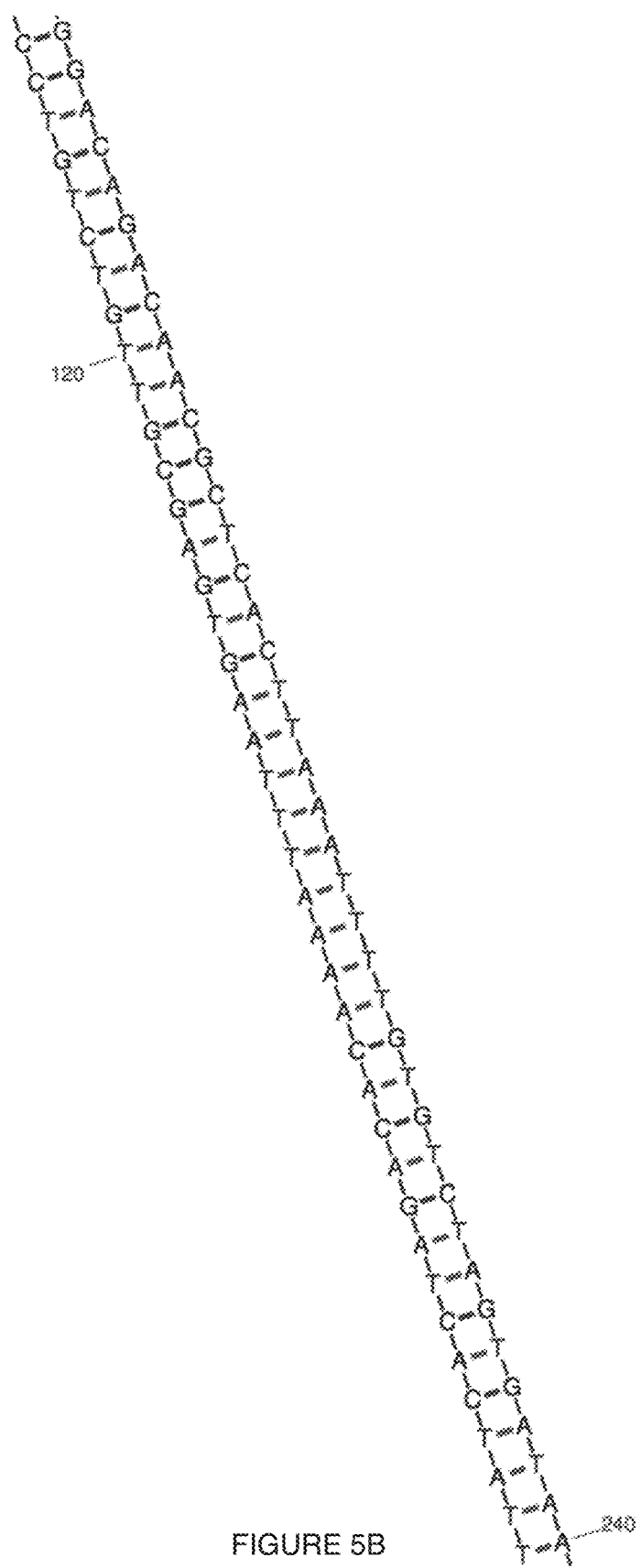
Figure 5C:
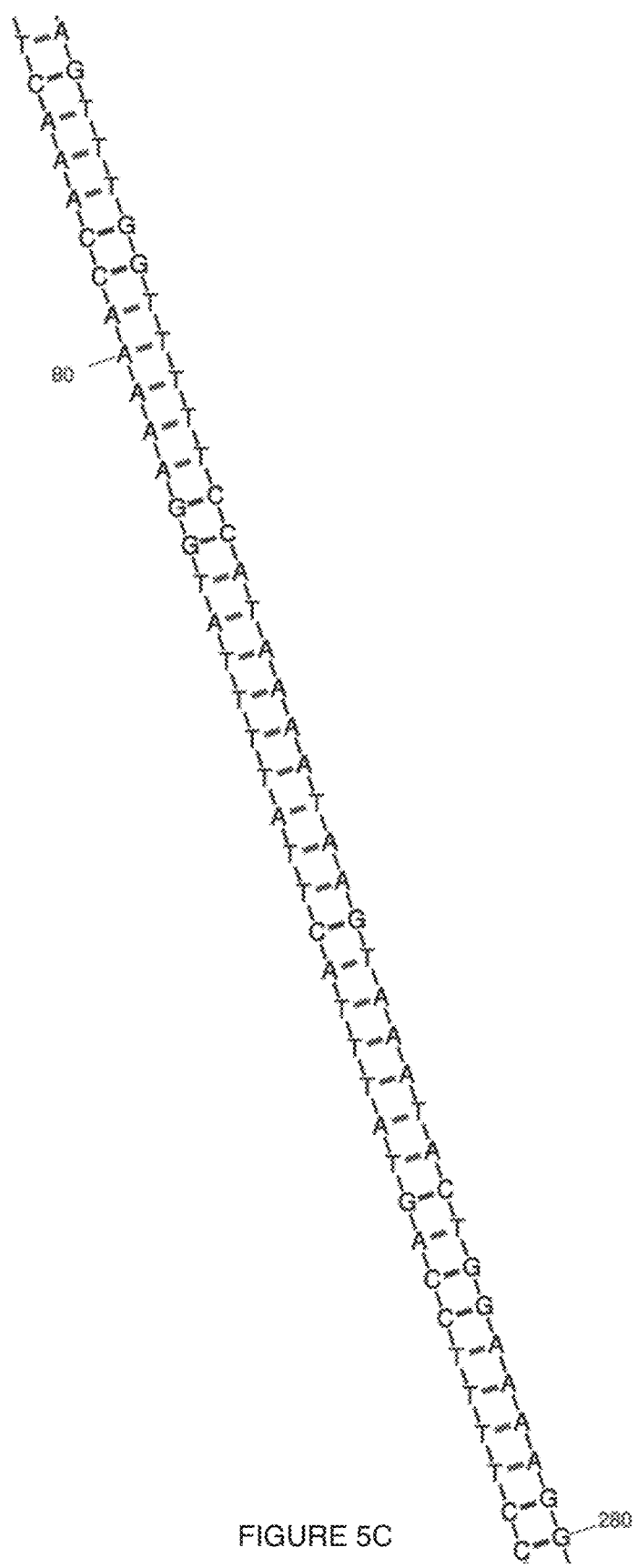
Figure 5D:
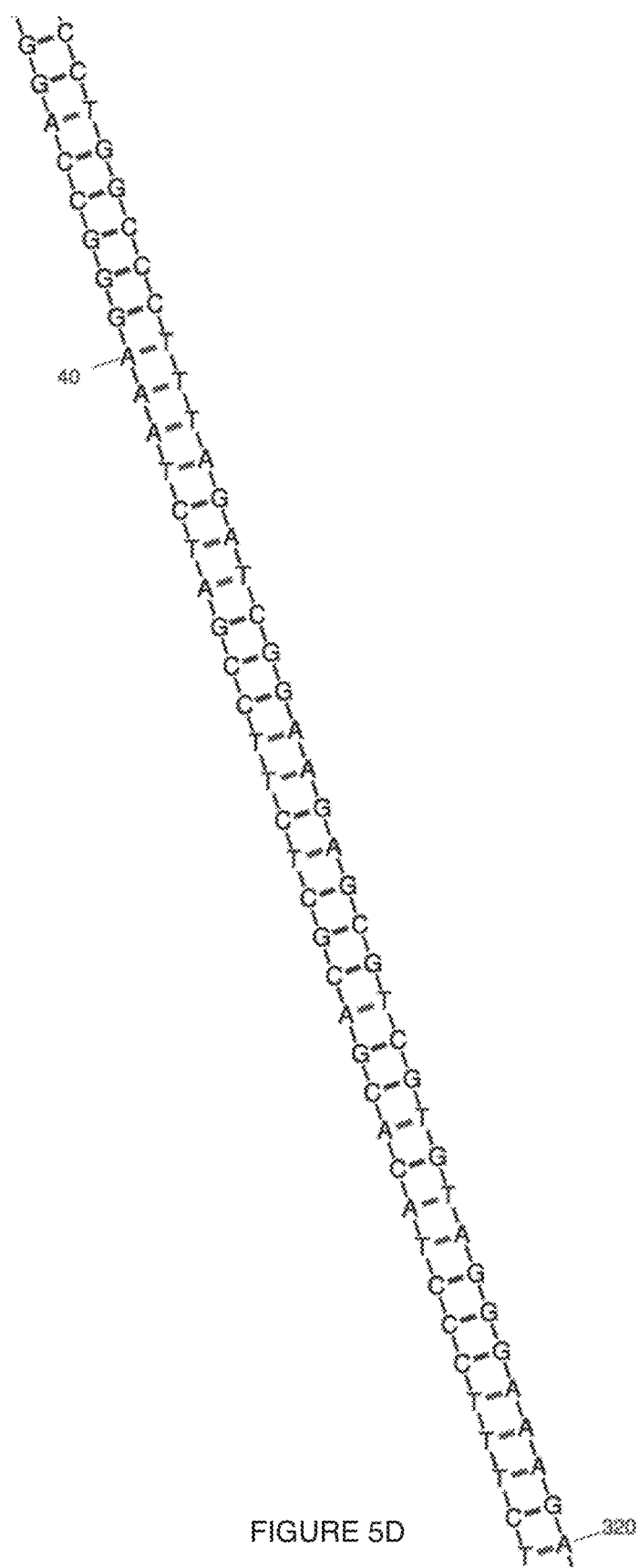
Figure 5E:
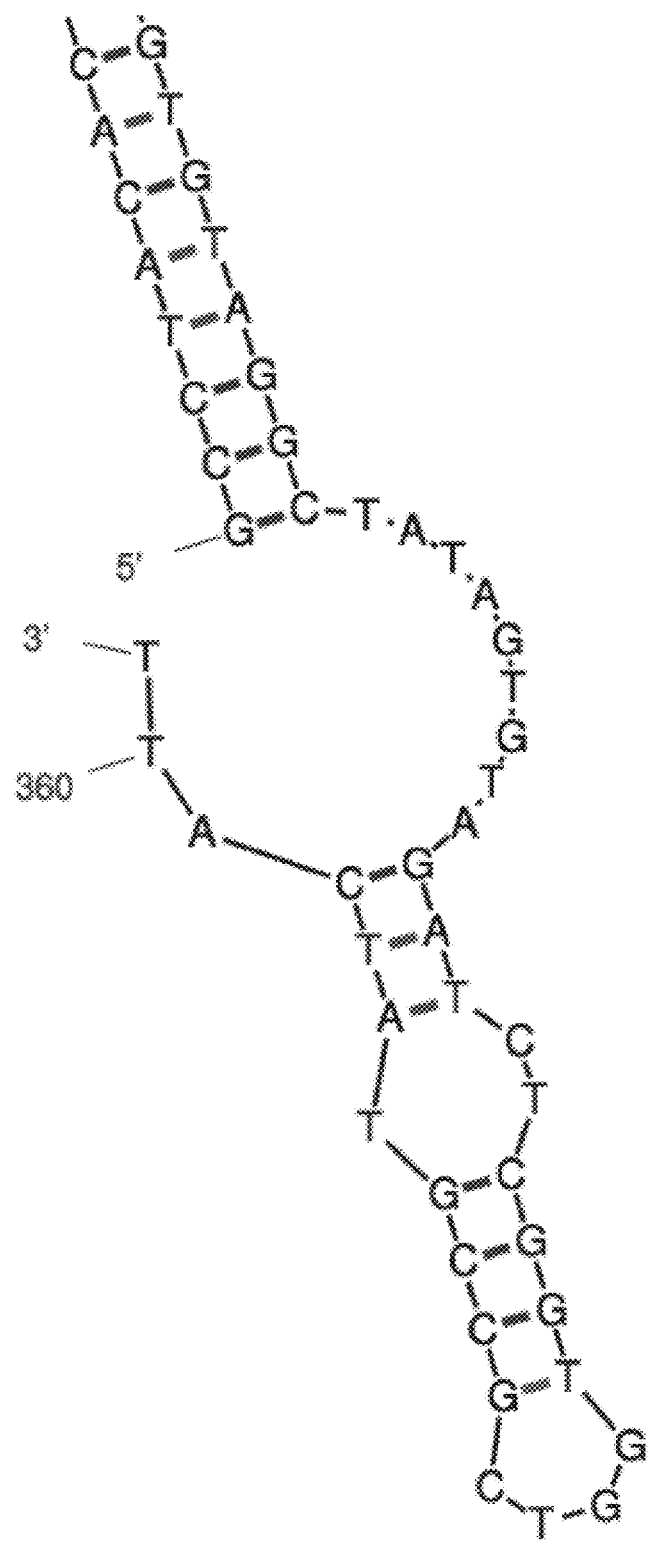

In a variation, adding one or more sequence regions (e.g., sequence repeats; etc.) can be based on one or more hairpin sequences (e.g., of primers, such as used in PCR amplification; etc.), such as where amplification with PCR primers including the one or more hairpin sequences can enable a plurality of nucleotide extension instances (e.g., through self-priming) for adding sequence repeats that can be Sanger sequenced. In an example, as shown in FIG. 3, adding one or more sequence repeats (e.g., to any suitable molecules; etc.) can include co-amplifying (and/or separately amplifying), with one or more sets of primers including one or more hairpin sequences (e.g., "chr21:14439076_PCR2_RP_hp", as shown in FIGS. 3 and 4), the set of target-associated molecules and nucleic acid molecules from the sample (e.g., maternal sample; biological sample; etc.), where the nucleic acid molecules include the target sequence region. In an example, primers (e.g., PCR primers) including a hairpin sequence can include one or more portions (e.g., sequence portions, structural portions; etc.) of a sequence shown in FIGS. 3 and 4 ("chr21:14439076_PCR2_RP_hp"). In an example, resulting products (e.g., resulting molecules, etc.) from adding one or more sequence regions (e.g., sequence repeats; etc.) based on or more hairpin sequences, can include one or more portions (e.g., sequence portions, structural portions; etc.) of sequences shown in FIGS. 5A-5E (e.g., where FIGS. 5A-5E illustrate a full sequence, with the sequence in FIG. 5A connected to the sequence in FIG. 5B, connected to the sequence in FIG. 5C, connected to the sequence in FIG. 5D, and connected to the sequence in FIG. 5E; etc.).

In examples, if a hairpin is used only at one end of the sequence (e.g., of a PCR primer sequence), a two-pass Sanger sequence is obtained (e.g., a chromatogram-related outputs including peak results for two passes of the sequence). In an example, a significant contribution of two-pass Sanger sequence is that the second sequence (e.g., second set of peak data and/or suitable chromatogram-related outputs for the sequence, etc.) can be more informative and cleaner in chromatogram content than the first-pass sequence (e.g., first set of peak data and/or suitable chromatogram-related outputs for the sequence, etc.) because of the decreased effect of primer-dimers at this increased length and because of the improved quality at longer lengths with Big Dye 3.1 chemistry. In examples, if a hairpin is used at both-ends, a plurality (e.g., many, multiple; etc.) rather than two (e.g., a plurality greater than two), Sanger chromatograms for the same sequence would be obtained; while this can significantly decrease any noise associated with abundance measurement due to averaging, it may not similarly decrease the effects of primer-dimers.

In a variation, hairpin sequences (e.g., of primers, etc.) can be configured for, generated for, used for, and/or otherwise processed without target-associated molecules and reference-associated molecules. For example, one or more sequence repeats (e.g., generated through amplification with PCR primers including one or more hairpin sequences) can be added to target molecules, reference molecules, and/or suitable molecules for enabling Sanger sequencing (and/or suitable sequencing technologies) of a particular sequence for a plurality of instances (e.g., multiple pass sequencing to enable multiple sets of data to be generated for the same sequence in a single sequencing run; etc.). In an example, the ratio of a major allele peak (e.g., peak intensity metric) (and/or suitable chromatogram-related output; etc.) to a minor allele peak (e.g., peak intensity metric) (and/or suitable chromatogram-related output; etc.) can be determined a plurality of times based on outputs from Sanger sequencing the sequence repeats (e.g., generated from use of hairpin sequences; etc.) to determine an overall abundance ratio. Additionally or alternatively, adding one or more sequence regions can be performed without processing of target-associated molecules and/or reference-associated molecules, such as a where adding the one or more sequence regions can independently improve (e.g., accuracy of; reduction of bias regarding; reduction of noise regarding; etc.) chromatogram-related outputs, abundance metrics, characterizations, and/or treatments.

However, hairpin sequences can be configured in any suitable manner, and adding one or more sequence regions based on hairpin sequences can be performed in any suitable manner.

In a specific example, as shown in FIGS. 13A-13B (e.g., illustrating generation of tandem repeats of around 150 base pair length amplicon to position spike-in bases into a predetermined Sanger quality window, such as a window facilitating improved sequencing outputs; where the amplicon mixture of endogenous and spike-in alleles can be circularized by LCR, and where tandem repeats can be then generated by RCA of the circularized amplicons, and where locations of the spike-in bases can be indicated by the shaded areas, and where the chromatograms can be generated from multiplex Sanger sequencing for multiple spike-in loci, and where amplicons originating from four loci were assembled into circular DNA by LCR, and the product was amplified by RCA and Sanger sequenced; etc.), adding sequence regions can include: performing ligation operations (e.g., Ligase Cycling Reaction with a Taq ligase and/or other suitable ligases; etc.) on an amplicon mixture generated from co-amplifying the target-associated nucleic acids and the target nucleic acids, thereby generating circularized amplicons; performing amplification operations (e.g., rolling circle amplification) on the circularized amplicons, thereby generating one or more modified sequences including sequence repeats (e.g., tandem repeats), and/or additional sequence regions identifying different targets, where the resulting spike-in mixture (e.g., including linear nucleic acids including the modified sequences) can be used in subsequent sequencing operations (e.g., Sanger sequencing, etc.). Adding sequence regions preferably includes adding sequence regions to a mixture of amplicons including target molecule-based amplicons (e.g., amplicons generated from endogenous target molecules) and target-associated molecule-based amplicons (e.g., amplicons generated from spike-in target-associated molecules). Alternatively, adding sequence regions can be performed on the target-associated molecules separately from the target molecules. Additionally or alternatively sequence regions can be initially generated (e.g., during generation of target-associated molecules, reference-associated molecules, etc.), such as to be part of the initial target-associated sequence and/or reference-associated sequence. Adding sequence regions and/or any suitable portions of embodiments of the method 100 can include performing any of the sample processing operations described herein, and/or other suitable operations. However, sequence regions can be configured in any suitable manner, and adding sequence regions can be performed in any suitable manner.

However, target-associated sequences, target sequences, and/or other suitable sequences can be modified in any suitable manner (e.g., deleting regions, modifying nucleotides at specific positions, etc.) using any suitable sample processing operations. However, generating spike-in mixtures S120 can be performed in any suitable manner.

2.3 Performing a Sequencing Operation.

Embodiments of the method 100 can include performing one or more sequencing operations S130 (e.g., on the one or more spike-in mixtures, etc.), which can function to sequence one or more components (e.g., one or more spike-in mixtures; etc.) and/or generate one or more sequencing outputs. Performing sequencing operations preferably includes performing Sanger sequencing (e.g., on a spike-in mixture, on target molecules separately, on target-associated molecules separately, etc.). Sanger sequencing preferably includes chain-termination approaches and/or any suitable operations related to Sanger sequencing (e.g., using labeled dideoxynucleotides and DNA polymerase, such as during in vitro DNA replication; generating a set of nucleic acid fragments covering base positions for bases of target-associated sequences, target sequences, reference-associated molecule sequences, reference sequences, any suitable sequences; performing analysis of the nucleic acid fragments, such as through capillary gel electrophoresis, laser detection of labelled bases; performing any suitable Sanger sequencing-related operations such as dye-terminator sequencing, automation and/or sample preparation associated with Sanger sequencing, microfluidic Sanger sequencing, computational processes to determine sequencing outputs; etc.). However, Sanger sequencing can be performed in any suitable manner.

Performing sequencing operations preferably includes sequencing one or more co-amplified spike-in mixtures (e.g., a spike-in mixture including co-amplified target-associated molecules and nucleic acids including an associated target sequence region; etc.), but can additionally or alternatively sequence any suitable components (e.g., separately sequencing target-associated molecules from a first sample and target molecules from a second sample; spike-in mixtures; samples from users; samples including reference-associated molecules and/or reference molecules; etc.) with any number of sequencing operations (e.g., any number of Sanger sequencing runs, etc.).

Figure 6A:
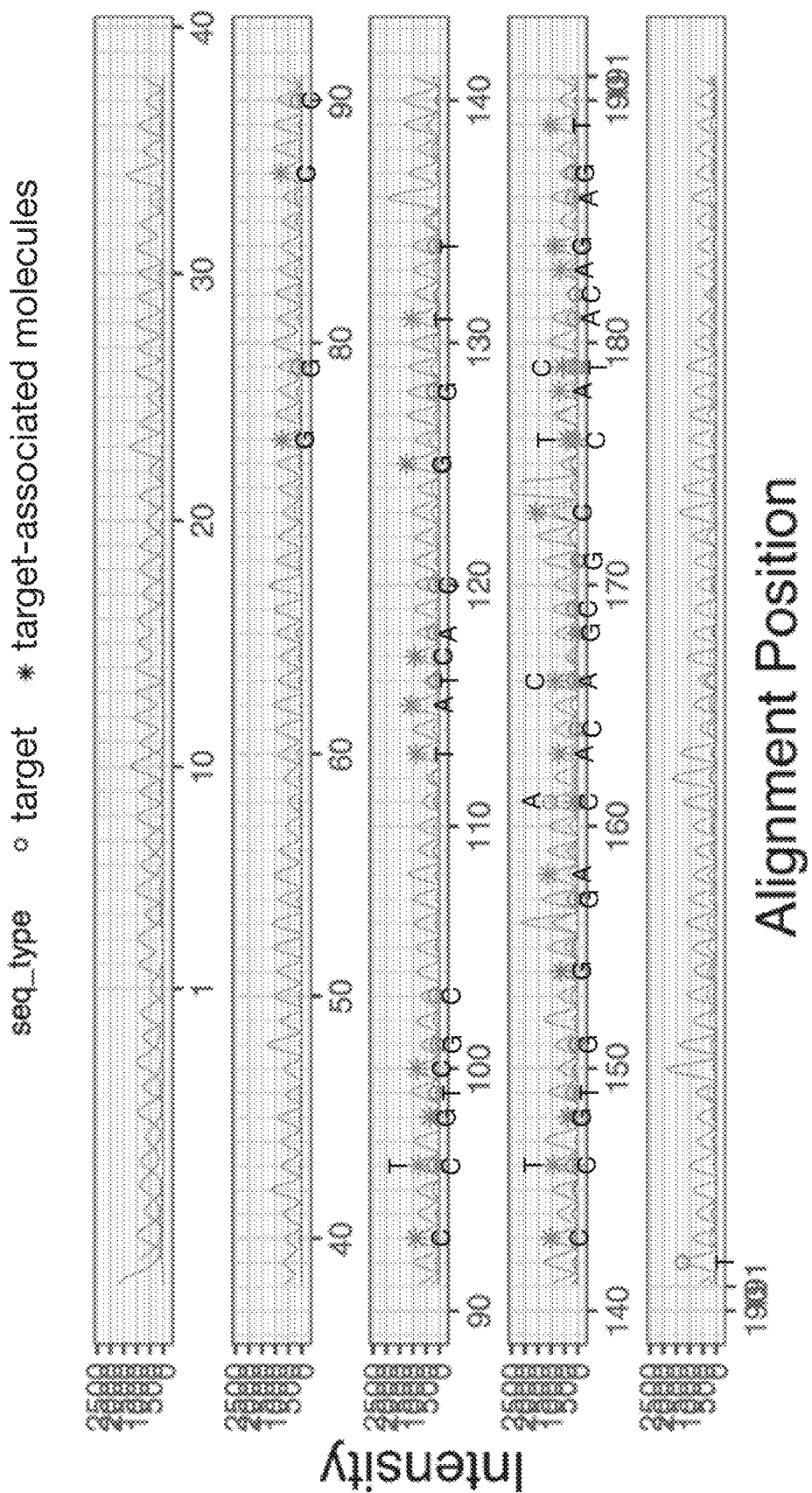
FIGS. 6A-6B include specific examples of chromatogram-related outputs and abundance metrics.
Figure 7A:
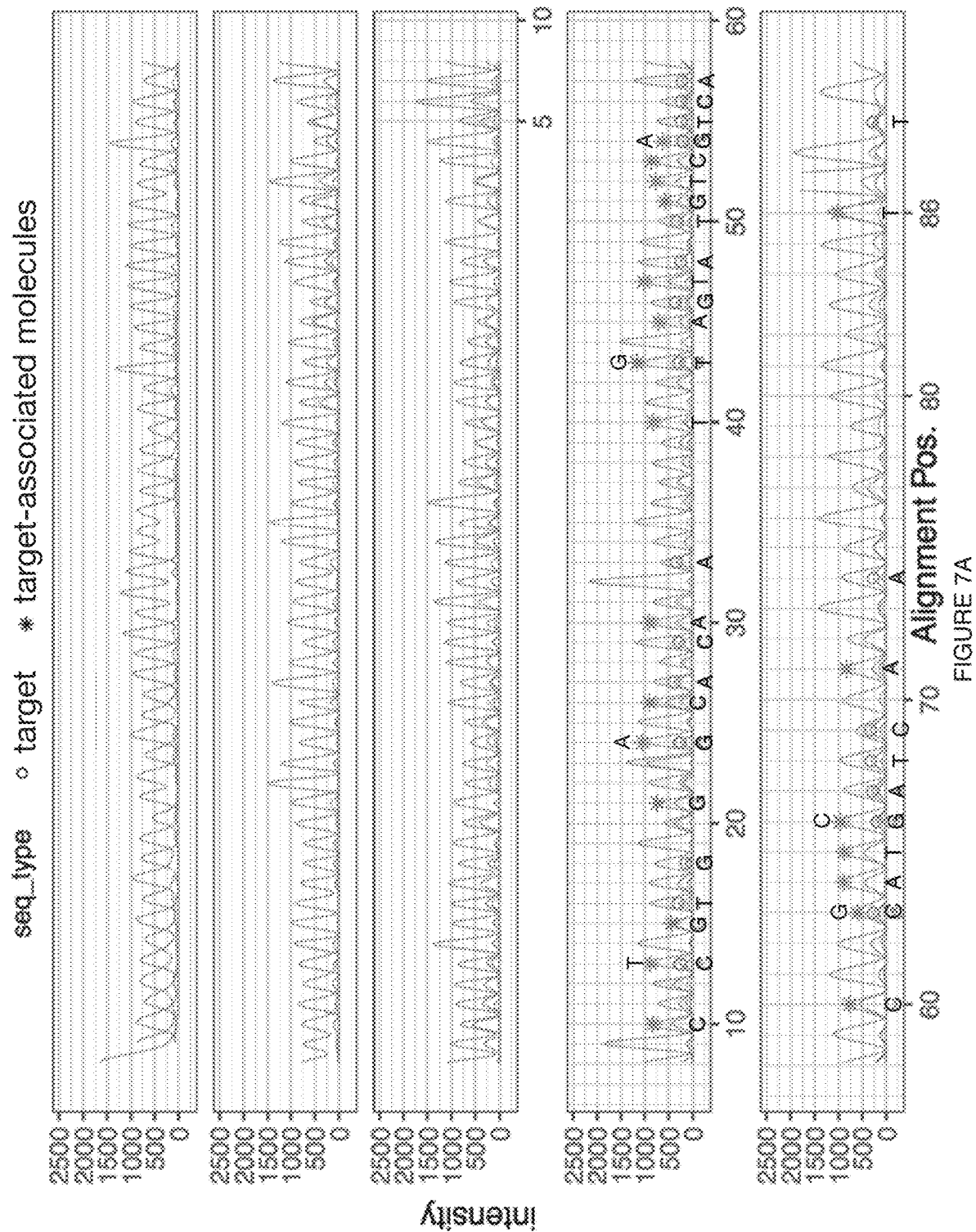
FIGS. 7A-7B include specific examples of chromatogram-related outputs and abundance metrics.
Figure 8:
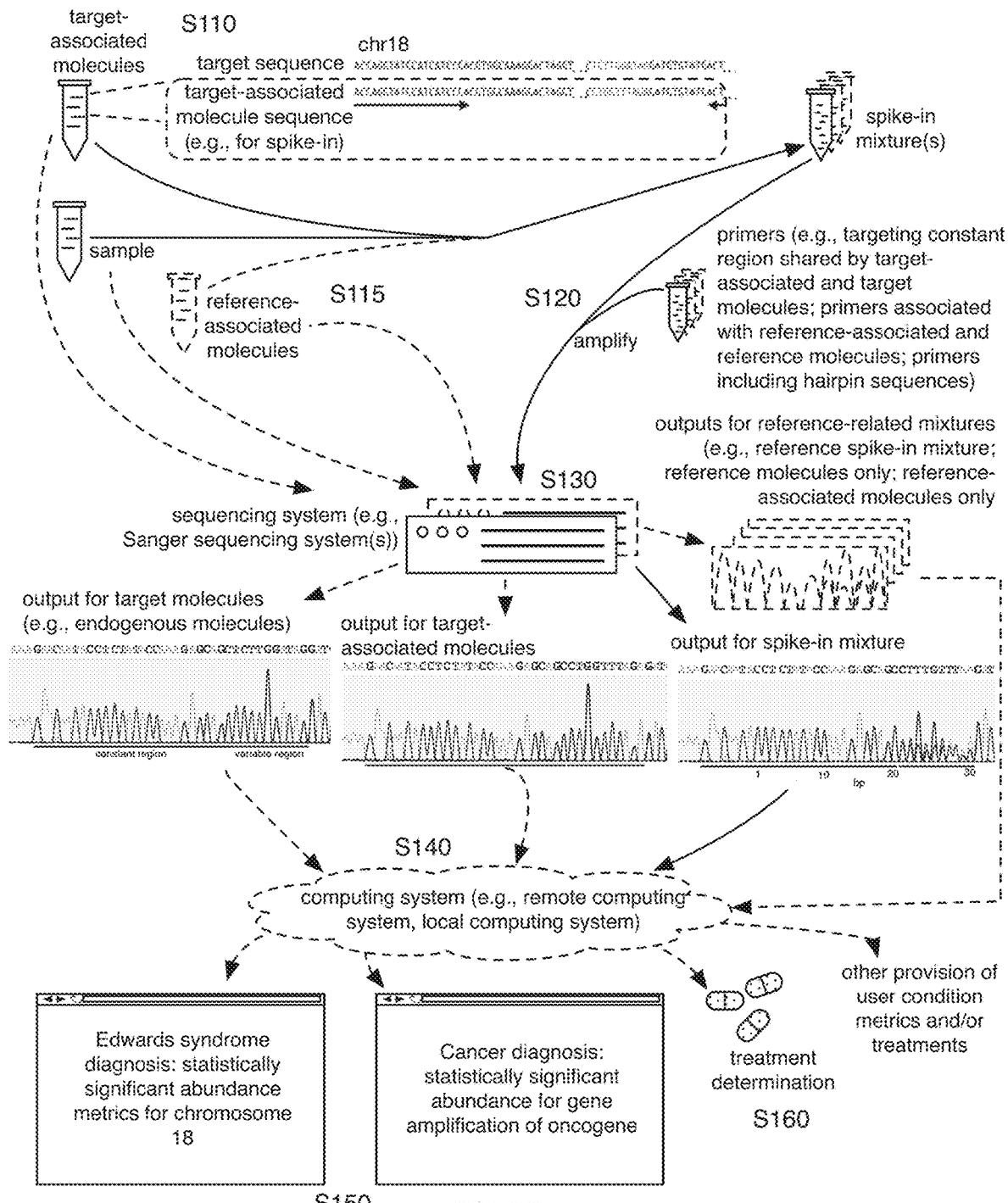
FIG. 8 includes a schematic representation of a variation of an embodiment of a method (specific example of target sequence=portion of SEQ ID NO: 11: specific example of target-associated molecule sequence=portion of SEQ ID NO: 12: specific example of output for target molecules=SEQ ID NO: 8: specific example of output for target-associated molecules=SEQ ID NO: g: specific example of output for spike-in-mixture=SEQ ID NO: 10)

Sequencing operations preferably can be performed to determine one or more sequencing outputs (e.g., quantitative sequencing outputs upon which abundance metrics can be determined; etc.). Sequencing outputs can include any one or more of: chromatogram-related outputs, sequence reads, high throughput sequencing outputs, text data, alignments, and/or any other suitable outputs from any suitable sequencing technologies. Chromatogram-related outputs can include any one or more of chromatograms (e.g., including peaks for sequenced bases of target-associated molecule sequences, target sequences, reference-associated molecule sequences, reference sequences, of any suitable associated regions, of any suitable molecules described herein; etc.), alignment positions (e.g., corresponding to peaks and/or bases sequenced by Sanger sequencing; each alignment position corresponding to one or more peaks and/or one or more bases; corresponding to bases of a plurality of aligned sequences, such as bases of a target-associated sequence and a target sequence; as shown in FIGS. 6A and 7A; etc.), any suitable sequencing-related positions, peak intensities, peak areas, peak similarities, peak differences, peak metrics relative peaks for the same or different base type; average intensity; median intensity; heights; widths; overlap and/or other comparisons between peaks of target-associated base and a target base at the same position or at a different position, text data (e.g., text results from the Sanger sequencing, etc.), and/or any other suitable outputs (e.g., related to Sanger sequencing, etc.). For example, as shown in FIG. 8, chromatogram-related outputs can include chromatograms for the different mixtures (e.g., a first chromatogram for the spike-in mixture, a second chromatogram for target-associated molecules alone, a third chromatogram for target molecules alone; etc.), such as where chromatogram peaks for different bases can be computationally processed to extract sequencing outputs.

Sequencing outputs (e.g., in relation to peaks for Sanger sequencing) for one or more particular bases can include a dependency on the number and/or type of bases preceding (and/or are otherwise related to) the particular base, where addition of sequence regions (e.g., sequence repeats) in generating the spike-in mixture can account for such dependencies. Additionally or alternatively, determining a variation region sequence for a target-associated sequence and/or a reference-associated molecule sequence can be based on the dependencies (e.g., on the number and/or type of preceding bases in the sequence, etc.) and/or other suitable sequencing parameters (e.g., characteristics of the sequencing technologies, such as characteristics of Sanger sequencing, etc.), such as where predetermined insertion and/or deletions for variation regions can enable calibration (e.g., auto-calibration) for being able to accurately compare peak intensities and/or other suitable chromatogram-related outputs in facilitating abundance metric determination. For example, the target variation region includes at least one of one or more insertions and one or more deletions, where the at least one chromatogram-related output includes alignment positions corresponding to the peaks (e.g., associated with bases of the first target-associated region, the target sequence region of the biological target, the target variation region, and the sequence region of the biological target, etc.), where, for each of the different pairs (e.g., a base of the target-associated sequence and a base of the target sequence, etc.) the base of the first target-associated sequence corresponds to a first alignment position that is different from a second alignment position corresponding to the base of the first target sequence (e.g., as shown in FIGS. 6A and 7A), and where the alignment positions of the at least one chromatogram-related output include the first and the second alignment positions.

In an example, the variation region can include predetermined shuffled bases (e.g., base substitutions, etc.) that can enable calibration and/or suitable processing operations (e.g., deconvolution, correction factor determination and application, etc.) for improved accuracy in abundance metric determination. However, determination of any suitable region and/or sequence can be based on any suitable sequencing parameters in any suitable manner. Additionally or alternatively, sequencing outputs for a particular base and/or other sequence region, and/or determination of any suitable region and/or sequence can be independent of other sequence regions and/or suitable sequencing parameters.

In variations, performing one or more sequencing operations can be for one or more products (e.g., components of spike-in mixtures; target-associated molecules, target molecules and/or other suitable molecules; etc.) with added sequence regions (e.g., sequence repeats; etc.), such as one or more products generated based on hairpin sequences (e.g., based on amplification with PCR primers including one or more hairpin sequences; etc.). Performing sequencing operations on products with sequence repeats can function to sequence one or more sequences and/or sequence regions a plurality of times, for generating additional sequencing outputs, which can reduce noise, be used to determine additional abundance metrics (e.g., for determining an overall abundance metric of improved accuracy; etc.), and/or for any suitable purposes (e.g., facilitating characterizations and/or treatments; etc.).

Additionally or alternatively, performing sequencing operations (and/or any suitable portions of embodiments of the method 100 and/or system 200) can include determining, applying, performing and/or otherwise using any suitable sequencing and/or sequencing-related technologies, such as high throughput sequencing, which can include and/or be associated with any one or more of: NGS, NGS-associated technologies, massively parallel signature sequencing, Polony sequencing, 454 pyrosequencing, Illumina sequencing, SOLiD sequencing, Ion Torrent semiconductor sequencing, DNA nanoball sequencing, Heliscope single molecule sequencing, Single molecule real time (SMRT) sequencing, Nanopore DNA sequencing, any generation number of sequencing technologies (e.g., second-generation sequencing technologies, third-generation sequencing technologies, fourth-generation sequencing technologies, etc.), amplicon-associated sequencing (e.g., targeted amplicon sequencing), metagenome-associated sequencing, sequencing-by-synthesis, tunneling currents sequencing, sequencing by hybridization, mass spectrometry sequencing, microscopy-based techniques, and/or any suitable technologies related to high throughput sequencing. Additionally or alternatively, sequencing and/or sequencing-related technologies can include any suitable technologies (e.g., capillary sequencing, etc.).

However, performing sequencing operations S130 can be performed in any suitable manner.

2.4 Determining an Abundance Metric.

Embodiments of the method 100 can include determining one or more abundance metrics S140 (e.g., for one or more samples; based on outputs of the one or more sequencing operations for the one or more spike-in mixtures, etc.), which can function to accurately determine abundance metrics, such as abundance metrics that can be meaningfully analyzed and compared (e.g., comparing individual abundances for a target molecule and a target-associated molecule to generate an abundance ratio, comparing abundance ratios for targets versus references; etc.), such as abundance metrics that can be used in facilitating characterizations and/or treatments. Abundance metrics can include any one or more of: abundance ratios (e.g., a ratio of first peak intensity metric for a first peak to a second peak intensity metric for a second peak, such as where the first and second peaks correspond to same or different alignment positions; ratios of any suitable sequencing output; a count ratio of an endogenous target molecule count to a target-associated molecule count; a sequencing output ratio of endogenous to spike-in, such as peak intensity metric ratio for a target sequence base and a corresponding target-associated sequence base; ratios with any suitable numerator and denominator; individual abundance ratios, such as usable in determining an overall abundance ratio and/or abundance metric; etc.), but can additionally or alternatively include individual abundances (e.g., individual peak intensities; counts; etc.), relative abundances, absolute abundances, and/or other suitable abundance metric. In a specific example, a ratio of endogenous molecules to spike-in molecules (e.g., ratio between endogenous DNA and spike-in DNA, etc.) can be calculated based on a sequencing output ratio (e.g., ratio of peak intensities for an endogenous-associated peak to a spike-in-associated peak) and a known abundance of spike-in molecules (e.g., used for generating the spike-in mixture).

Determining abundance metrics is preferably based on one or more sequencing outputs, but can additionally or alternatively be based on any suitable data (e.g., supplementary data including known abundances, biometric data, medical history data, demographic data, genetic history, survey data, dietary data, behavioral data, environmental data, sample type, and/or other suitable contextual data). For example, determining abundance ratios (e.g., target-associated abundance ratios; etc.) (and/or any suitable abundance metrics) can be based on one or more chromatogram-related outputs including one or more peak intensities, peak areas, peak metrics for bases sharing a base type, peak metrics for bases with different base types and/or any other suitable chromatogram-related outputs and/or sequencing outputs. Determining abundance metrics can include computational processing (e.g., with a remote computing system such as a cloud computing system, with a local computing system, etc.), such as computationally processing one or more sequencing outputs (e.g., chromatograms, peak data, etc.) and/or other suitable data, but can additionally or alternatively include any suitable processing (e.g., manual processing; etc.). Processing (e.g., for determining abundance metrics; etc.) and/or suitable portions of embodiments of the method 100 (e.g., facilitating characterizations and/or treatments, etc.) can include any one or more of can include any one or more of: performing statistical estimation on data (e.g. ordinary least squares regression, non-negative least squares regression, principal components analysis, ridge regression, etc.), deconvolving (e.g., of overlapping peaks from a chromatogram, of peaks with inadequate resolution, of any suitable peaks; Fourier deconvolution; Gaussian function-based deconvolution; Lucy-Richardson deconvolution etc.), extracting features (e.g., for any suitable number of peaks of a chromatogram, etc.), performing pattern recognition on data, fusing data from multiple sources, combination of values (e.g., averaging values, etc.), compression, conversion (e.g., digital-to-analog conversion, analog-to-digital conversion), wave modulation, normalization, updating, ranking, validating, filtering (e.g., for baseline correction, data cropping, etc.), noise reduction, smoothing, filling (e.g., gap filling), aligning, model fitting, windowing, clipping, transformations, mathematical operations (e.g., derivatives, moving averages, summing, subtracting, multiplying, dividing, etc.), multiplexing, demultiplexing, interpolating, extrapolating, clustering, other signal processing operations, other image processing operations, visualizing, and/or any other suitable processing operations.

In variations, determining abundance metrics can be based on and/or otherwise associated with one or more sequencing outputs associated with target-associated sequences (and/or reference-associated sequences) including variation regions with one or more insertions (e.g., nucleotide insertions; etc.) and/or one or more deletions (e.g., nucleotide deletions; etc.) and/or any suitable modifications. For example, determining a set of target-associated abundance ratios can be based on a set of peaks (e.g., peak intensity data for peaks corresponding to sequenced bases of a target sequence and a target-associated sequence; etc.) and at least one of the substitution, the insertion, and the deletion (e.g., characteristics of the one or more substitutions, insertions, and/or deletions; such as size of the modification, in relation to number of nucleotides; types of modification such as in relation to base type changes; positions of where the modifications are applied; etc.). As shown in FIGS. 6A and 7A, variation regions including one or more insertions and/or deletions can result in shifted alignment positions (e.g., for bases of the target-associated sequence, relative bases a target sequence; such as where the sequence similarity between bases of a target-associated region and a target sequence region can be shifted in relation to position due to the one or more insertions and/or deletions; etc.). In an example, the target variation region (e.g., of a target-associated sequence; etc.) can include at least one of an insertion and a deletion, where the one or more chromatogram-related outputs can include alignment positions corresponding to a set of peaks (e.g., peak data for and/or associated with the target-associated region of the target-associated molecules, the target sequence region of the biological target, the target variation region of the target-associated molecules, and the sequence region of the biological target, etc.), and where determining the set of target-associated abundance ratios (and/or suitable abundance metrics) includes, for each of the different pairs (e.g., of a base of the target-associated sequence and a base of the target sequence; etc.): determining a peak intensity metric (e.g., a maximum intensity for the peak; an overall intensity for the peak; etc.), at a first alignment position of the alignment positions, for the base of the target-associated sequence of the pair, based on the at least one chromatogram-related output (e.g., based on peak intensity data for the sequenced bases; based on a chromatogram; etc.); determining a peak intensity metric, at a second alignment position of the alignment positions, for the base of the target sequence of the pair, based on the at least one chromatogram-related output (e.g., based on peak intensity data for the sequenced bases; based on a chromatogram; etc.), where the first alignment position is different from the second alignment position, and where the alignment positions include the first and the second alignment positions; and/or determining a target-associated abundance ratio (and/or suitable abundance metric; etc.) of the set of target-associated abundance ratios (and/or set of suitable abundance metrics; etc.), based on the peak intensity metric for the base of the target-associated sequence and the peak intensity metric for the base of the first target sequence. In an example, as shown in FIGS. 6A and 7A, the first alignment position can correspond to a first peak and a second peak (e.g., overlapping peaks corresponding to the same alignment position; corresponding to same or different base types; etc.) of the first set of peaks, where the first peak corresponds to an overlapping base of the target-associated sequence (e.g., where target-associated sequence bases are marked by a "*" as shown in FIGS. 6A and 7A), where the first peak corresponds to a first target-associated abundance ratio (e.g., for a pair of the overlapping base of the target-associated sequence and a corresponding base, shifted in alignment position, of the target sequence, where the amount of shift in alignment position is based on the characteristics of the one or more insertions and/or deletions, such as the sizes of the one or more insertions and/or deletions; etc.) of the set of target-associated abundance ratios, where the second peak corresponds to an overlapping base of the target sequence (e.g., where target sequence bases are marked by a "O" as shown in FIGS. 6A and 7A), and/or where the second peak corresponds to a second target-associated abundance ratio (e.g., distinct from the first target-associated abundance ratio; for a pair of the overlapping base of the target sequence and a corresponding base, shifted in alignment potion, of the target-associated sequence; etc.) of the set of target-associated abundance ratios.

Figure 6B:
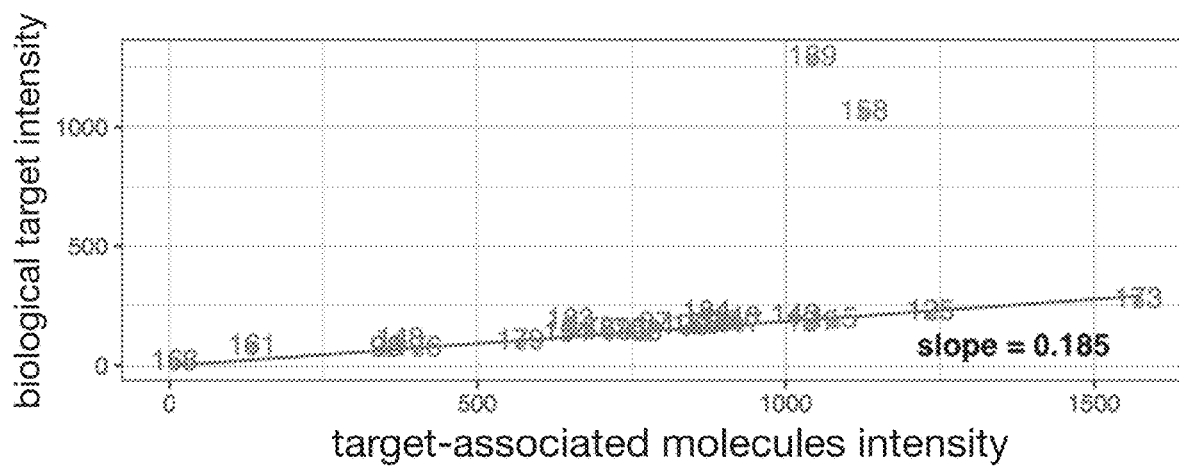

In a specific example, as shown in FIGS. 6A-6B, the initial abundance of sample DNA for the region chr21: 15811326-15811417 can be determined by estimating the ratio of hg19 "reference" DNA intensity to spike-in "Spk" intensity (e.g., after Sanger sequencing of a spike-in mixture generated from co-amplification of target-associated molecules and target molecules including the target sequence; etc.); where the target-associated sequence (e.g. spike-in sequence; of the target-associated molecules; etc.) includes a three nucleotide deletion, resulting in a three-position shift in alignment position for corresponding (e.g., sequence similar; etc.) pairs of a base form the target-associated sequence and the target sequence; where individual target-associated abundance ratios can be determined based on peak intensities (e.g., indicated by positions of the "*"s and "O"s at peaks of the chromatogram) of the corresponding pairs (e.g., where an individual abundance ratio for alignment position 161, corresponding to a "C" base of a target-associated sequence and indicated by a "*", can be determined based on a ratio of a peak intensity metric (e.g., maximum intensity for the peak) for the "C" base of the target-associated sequence and a peak intensity metric (e.g., maximum intensity for the peak) for the "C" base of the target sequence, indicated by a "O" and at position 164 due to an alignment position shift from the three nucleotide deletion in the variation region of the target-associated sequence; etc.), such as where the target-associated ratios can be plotted (e.g., as shown in FIG. 6B; such as where the individual abundance ratio for the pair of "C" bases at positions 161 and 164, respectively, is indicated by the alignment position number "161" in the plot; etc.), and/or such as where the slope of the data points (e.g., 0.185; the linear regression for the target-associated abundance ratio data points; of the plot; etc.) can be an abundance metric describing abundance of the target molecules in the sample relative to the abundance of the target-associated molecules (e.g., abundance of endogenous DNA to spike-in DNA; sample DNA was abundant at 0.185 the level of the spike-in DNA; etc.).

Figure 7B:
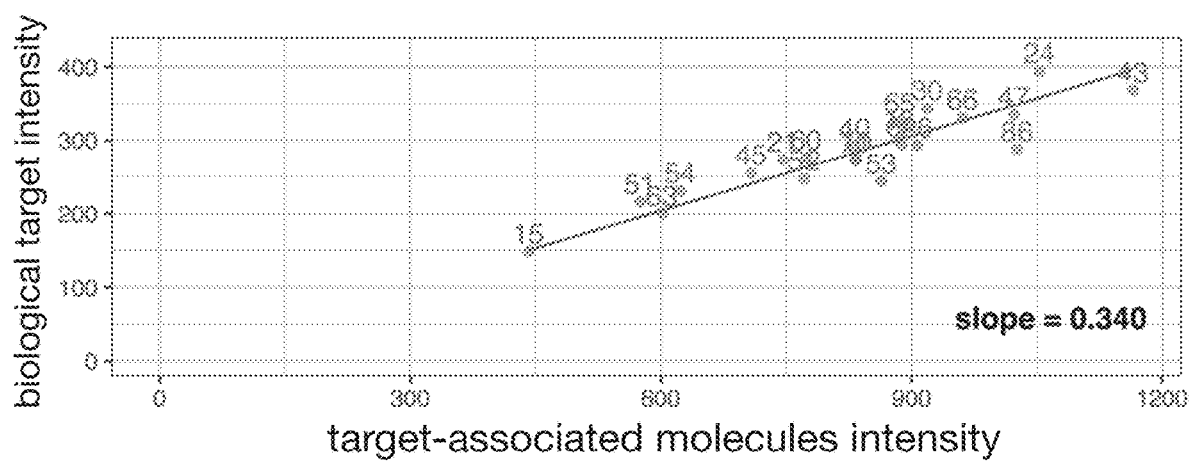

In a specific example, as shown in FIGS. 7A-7B, the initial abundance of sample DNA for the region chr21: 22231528+22231612 can be determined by estimating the ratio of hg19 "reference" DNA intensity to spike-in "Spk" intensity (e.g., after Sanger sequencing of a spike-in mixture generated from co-amplification of target-associated molecules and target molecules including the target sequence; etc.); where the target-associated sequence (e.g. spike-in sequence; of the target-associated molecules; etc.) includes a three nucleotide deletion, resulting in a three-position shift in alignment position for corresponding (e.g., sequence similar; etc.) pairs of a base form the target-associated sequence and the target sequence; where individual target-associated abundance ratios can be determined based on peak intensities (e.g., indicated by positions of the "*"s and "O"s at peaks of the chromatogram) of the corresponding pairs (e.g., where an individual abundance ratio for alignment position 15, corresponding to a "G" base of a target-associated sequence and indicated by a "*", can be determined based on a ratio of peak intensity metric (e.g., maximum intensity for the peak) for the "G" base of the target-associated sequence and a peak intensity metric (e.g., maximum intensity for the peak) for the "G" base of the target sequence, indicated by a "O" and at position 18 due to an alignment position shift from the three nucleotide deletion in the variation region of the target-associated sequence; etc.), such as where the target-associated ratios can be plotted (e.g., as shown in FIG. 7B; such as where the individual abundance ratio for the pair of "G" bases at positions 15 and 18, respectively, is indicated by the alignment position number "15" in the plot; etc.), and/or such as where the slope of the data points (e.g., 0.34; the linear regression for the target-associated abundance ratio data points; of the plot; etc.) can be an abundance metric describing abundance of the target molecules in the sample relative to the abundance of the target-associated molecules (e.g., abundance of endogenous DNA to spike-in DNA; sample DNA was abundant at 0.34 the level of the spike-in DNA; etc.).

However, determining abundance metrics based on and/or otherwise associated with sequencing outputs associated with variation regions including one or more insertions, deletions, and/or suitable modifications, can be performed in any suitable manner.

In a variation, extracting abundance metrics can include deconvolving overlapping peaks (e.g., chromatogram peaks, etc.) including a first peak corresponding to a target-associated sequence base (e.g., an "A" base) at a variation region position, and a second peak corresponding to a target sequence base (e.g., a "T" base) at the position; and calculating sequencing outputs and/or abundance metrics for the deconvolved peaks (e.g., a ratio of peak intensities for the "T" base to the "A" base). In a variation, deconvolution can be for overlapping peaks between a base of a first loci (e.g., chromosome 18) and a base of a second loci (e.g., of the same chromosome, of a different chromosome such as chromosome 21, etc.).

In a variation, as shown in FIG. 8, statistical estimation of the relative abundances of target and target-associated sequences from a spike-in mixture chromatogram can be based on a first chromatogram (and/or any suitable sequencing outputs such as peak data; etc.) for target molecules alone and/or a second chromatogram (and/or any suitable sequencing outputs; etc.) for target-associated molecules alone (e.g., where peaks for a particular base across chromatograms and/or sets of sequencing outputs can be processed for multiple linear regression; etc.). In a variation, deconvolution (e.g., Lucy-Richardson deconvolution) can be applied to resolve peaks of a chromatogram (e.g., achieving improved separation between peaks of the same color) and/or to resolve other suitable outputs. In a specific example, the method 100 can include: generating a set of chromatograms (and/or chromatogram-related data; etc.) (e.g., for the spike-in mixture, for the target-associated molecules alone, for the target molecules alone, etc.); resolving peaks of the set of chromatograms through deconvolution (e.g., where this and/or other suitable operations can be omitted; etc.); and performing regression analyses on the processed chromatograms. Additionally or alternatively, deconvolution, regression analyses, or other computational operations can be performed for any suitable number and combination of chromatogram peaks and/or other components of sequencing system outputs.

In a variation, determining an abundance metric can include determining an overall abundance metric from a plurality of individual abundance metrics, which can increase the accuracy of the abundance metric. In an example, the method 100 can include determining at least one chromatogram-related output based on Sanger sequencing associated with the first set of target-associated molecules (e.g., including a first target-associated sequence including a first target-associated region with sequence similarity to a first target sequence region of a first target sequence; etc.), the set of target molecules, and a second set of target-associated molecules, where the second set of target-associated molecules includes a second target-associated sequence including a second target-associated region with sequence similarity to a second target sequence region of a second target sequence; determining a first set of target-associated abundance ratios for different sets of bases of the first target-associated sequence and the first target sequence (e.g., where each different set of bases, from the different sets of bases, includes at least one base of the first target-associated sequence and at least one base of the first target sequence; etc.), based on the at least one chromatogram-related output; determining a second set of target-associated abundance ratios for different sets of bases of the second target-associated sequence and the second target sequence (e.g., where each different set of bases, from the different sets of bases, includes at least one base of the second target-associated sequence and at least one base of the second target sequence, etc.) based on the at least one chromatogram-related output; and/or determining one or more overall abundance metric (e.g., describing an abundance of the biological target for the sample, etc.) based on the first and the second sets of target-associated abundance ratios. In an example, the first target sequence can correspond to a first loci of a chromosome, where the second target sequence can correspond to a second loci of the chromosome, and where facilitating characterization of the one or more conditions can include facilitating characterization of a chromosomal abnormality based on the one or more overall abundance metric.

For example, as shown in FIG. 9, determining an overall abundance ratio metric can be based on: determining individual sequencing output ratios for each position of a variation region based on sequencing outputs (e.g., peak intensities, etc.) for pairs of an endogenous-associated peak and a corresponding spike-in-associated peak for bases at the position, where the individual sequencing output ratios can span any number of base positions, across any number of loci (e.g., where individual sequencing output ratios for different loci are extracted from different chromatograms for the different loci; where the ratios are extracted from the same chromatogram including data for a plurality of loci; etc.), chromosomes, targets, and/or other suitable aspects; and combining the individual sequencing output ratios (e.g., averaging). Additionally or alternatively, determining overall abundance metrics from individual abundance metrics can leverage any suitable statistical approach (e.g., averaging, median, etc.), and/or can be performed in any suitable manner. In a variation, different sets of abundance metrics can be determined for separately prepared and/or sequenced samples (e.g., for a first sample including target-associated molecules, and a second sample including target molecules, where the first and second samples can be separately prepared and/or sequenced such as Sanger sequenced; etc.). For example, the method 100 can include Sanger sequencing (e.g., performed by a first party, a third party, a user, and/or any suitable entity; etc.) including: Sanger sequencing of a first sample including a set of target-associated molecules; and Sanger sequencing of a second sample including the set of target molecules, where determining the at least one chromatogram-related output (e.g., a set of peak intensities; chromatograms; etc.) can include: determining a first chromatogram-related output (e.g., a chromatogram, a set of peak intensities; etc.) associated with the set of target-associated molecules (e.g., peak intensity data for bases of a target-associated sequence of the set of target-associated molecules; etc.), based on the Sanger sequencing of the first sample; and determining a second chromatogram-related output (e.g., a chromatogram, a set of peak intensities; etc.) associated with the set of target molecules (e.g., peak intensity data for bases of a target-associated sequence of the set of target-associated molecules; etc.), based on the Sanger sequencing of the second sample, and where determining a set of target-associated abundance ratios (and/or any suitable abundance metrics) can include determining the set of target-associated abundance ratios based on the first chromatogram-related output and the second chromatogram-related output (e.g., determining a first set of individual abundance ratios for the set of target-associated molecules based on the first chromatogram-related output; determining a second set of individual abundance ratios for the set of target molecules based on the second chromatogram-related output; where an overall abundance ratio can be determined based on the individual abundance ratios; etc.).

In a variation, abundance metrics can be determined over time (e.g., for different samples collected over time; by performing multiple instances of embodiments of the method 100 over time; etc.), where the series of abundance metrics can be analyzed in facilitating one or more characterizations of one or more conditions (e.g., monitoring cancer-associated molecule count over time; etc.), treatments (e.g., evaluating cancer treatment efficacy over time; etc.), and/or other suitable information. For example, the method 100 can include, where one or more conditions (e.g., medical conditions, etc.) can include at least one of a single gene disorder and a cancer condition (and/or any suitable conditions; etc.); determining a first overall abundance metric (and/or any suitable first abundance metric; etc.) (e.g., describing a first abundance of the biological target; etc.) associated with a first time period (e.g., associated with a first instance of performing one or more portions of embodiments of the method 100; etc.); determining a second overall abundance metric (e.g., describing a second abundance of the biological target; etc.) where the second overall abundance metric is associated with a second time period (e.g., associated with a second instance of performing one or more portions of embodiments of the method 100; etc.); and/or facilitating the characterization of the one or more conditions based on the first overall abundance metric (e.g., based on a first comparison between the first overall abundance metric and a first reference-associated abundance metric such as a first overall reference-associated abundance metric; etc.) and the second overall abundance metric (e.g., a second comparison between the second overall abundance metric and a second overall reference-associated abundance metric describing a second abundance of the same biological reference or a different biological reference, where the second overall reference-associated abundance metric can be associated with the second time period and/or any suitable time period; a second comparison between the second overall abundance metric and the first overall reference-associated abundance metric, etc.).

In a variation, determining an abundance metric can include applying an abundance determination model including any one or more of: probabilistic properties, heuristic properties, deterministic properties, and/or any other suitable properties.

However, determining abundance metrics S140 can be performed in any suitable manner.

2.5 Processing Reference-Associated Molecules.

Additionally or alternatively, embodiments of the method 100 can include processing a set of reference-associated molecules (e.g., including a reference sequence including a reference-associated region and a reference variation region, such as where the sequences and/or regions are analogous to the sequence and/or regions of target-associated molecules, such as where such molecules, sequences and/or regions can be configured, generated, applied, processed, and/or used in analogous manners, such as in a manner analogous to that described in relation to Sino, S120, and/or herein; etc.); S115, which can function to generate and/or process (e.g., through applying one or more suitable portions of embodiments of the method 100, etc.) molecules associated with reference molecules (e.g., reference nucleic acids including a reference sequence identifying a reference chromosome, such as chromosome 21; reference nucleic acids including a reference sequence associated with wildtype versions for single gene disorders; etc.), such as reference molecules present in a sample (e.g., the biological sample from which target molecules are extracted; etc.), such as to determine reference abundance metrics (e.g., reference-associated abundance metrics; etc.) that can be compared to abundance metrics for targets (e.g., in determining relative abundance; compared to target-associated abundance metrics; etc.) and/or otherwise processed (e.g., for facilitating characterization and/or treatments; etc.) such as by comparing an abundance ratio for target chromosome 21 to an abundance ratio for reference chromosome 18 to screen for trisomy 21 and/or trisomy 18. Processing reference-associated molecules (e.g., generating the molecules; processing the molecules to generate reference spike-in mixtures; sequencing; computational processing, etc.) and/or reference molecules can be performed in any manner analogous to processing the target-associated molecules, target molecules, and/or other suitable components. However, processing reference-associated molecules S115 can be performed in any suitable manner.

2.6 Facilitating Characterization of a Condition.

Additionally or alternatively, embodiments of the method 100 can include facilitating characterization of one or more conditions S150 (e.g., medical conditions such as genetic disorders; based on one or more abundance metric; etc.), which can function to detect, diagnose, analyze, determine characterizations for, aid one or more care providers in relation to, provide data (e.g., parameters; etc.) regarding; and/or otherwise facilitate characterization of one or more conditions.

Characterizations can include any one or more of: diagnoses, risk assessments, causes (e.g., identification of user behaviors, demographics, medical history, genetics, and/or other suitable aspects contributing to the condition), and/or other suitable information informative of the one or more conditions. In variations, one or more characterizations can be used in any one or more of: determining a treatment, informing users, informing care providers (e.g., guiding care provider in diagnoses; etc.), and/or performing any suitable operations. Facilitating one or more characterizations is preferably based on comparisons of abundance ratios (e.g., a comparison of an overall target-associated abundance ratio against an overall reference-associated abundance ratios), but can additionally or alternatively be based on any number and/or type of abundance metrics (e.g., any suitable analytical techniques, such as statistical estimation analyses, applied to and/or used in generating the abundance metrics; etc.), but can be additionally or alternatively based on any suitable abundance metrics. In an example, the biological target can be associated with one or more medical condition, and facilitating characterization of the one or more medical conditions can be based on a comparison between a first overall abundance metric (e.g., an overall target-associated abundance metric; etc.) and a second overall abundance metric (e.g., an overall reference-associated abundance metric describing abundance of a biological reference; etc.).

In an example, the condition (e.g., medical condition; etc.) can include a genetic disorder including at least one of a chromosomal abnormality and a single gene disorder; where a first target sequence region (e.g., of a first target sequence of a first set of target-associated molecules; etc.) can be associated with at least one of a first chromosome and a mutation; where a reference sequence region of the biological reference is associated with at least one of a second chromosome and a lack of the mutation; and/or where facilitating prenatal diagnosis (and/or suitable characterizations; etc.) of the genetic disorder includes facilitating the prenatal diagnosis of the at least one of the chromosomal abnormality and the single gene disorder based on the comparison between an overall target-associated abundance ratio (e.g., determined based on a first set of target-associated abundance ratios corresponding to peak intensities of a different pair of a base of the first target-associated sequence and a base of the first target sequence; etc.) and a reference-associated overall abundance ratio (e.g., determined based on a set of reference-associated abundance ratios corresponding to peak intensities of a different pair of a base of the reference-associated sequence and a base of the reference sequence; etc.). In an example, the condition can include a genetic disorder including the chromosomal abnormality, where the first target sequence corresponds to a first loci of the first chromosome, and where the method 100 can include generating a second set of target-associated molecules includes a second target-associated sequence including a second target-associated region with sequence similarity to a second target sequence region of a second target sequence corresponding to a second loci of the first chromosome; and determining a second set of target-associated abundance ratios based on the at least one chromatogram-related output, where each target-associated abundance ratio, of the second set of target-associated abundance ratios, corresponds to a different pair of a base of the second target-associated sequence and a base of the second target sequence, where determining the overall target-associated abundance ratio includes determining the overall target-associated abundance ratio based on the first set of target-associated abundance ratios and the second set of target-associated abundance ratios, and where the reference sequence region of the biological reference is associated with the second chromosome.

In an example, the condition (e.g., medical condition; etc.) can include at least one of one or more chromosomal abnormalities, one or more single gene disorders, and/or one or more cancer conditions, where a target sequence region is associated with at least one of a first chromosome (e.g., associated with the chromosomal abnormality; associated with the cancer condition; etc.) and a mutation (e.g., associated with the chromosomal abnormality; associated with the cancer condition; etc.), where a reference sequence region of the biological reference is associated with at least one of a second chromosome and a lack of the mutation, and/or where facilitating the characterization of the medical condition includes facilitating the characterization of the at least one of one or more chromosomal abnormalities, one or more single gene disorders, and/or one or more cancer conditions, based on one or more abundance metrics (e.g., a set of target-associated abundance ratios and a set of reference-associated abundance ratios, such as an overall target-associated abundance ratios determined from the set of target-associated abundance ratios, and an overall reference-associated abundance ratio determined from the set of reference-associated abundance; etc.).

In variations, facilitating one or more characterizations can be based on one or more fetal fraction measurements (and/or any other suitable data, such as one or more abundance metrics; etc.). For example, facilitating prenatal diagnosis can include facilitating the prenatal diagnosis of one or more genetic disorder based on a fetal fraction measurement and/or one or more abundance metrics (e.g., an overall target-associated abundance ratio, a reference-associated overall abundance ratio, a comparison between the ratios, etc.). However, facilitating characterizations based on fetal fraction measurements can be performed in any suitable manner.

Facilitating characterization of one or more conditions and/or any other suitable portions of embodiments of the method 100 (e.g., determining abundance metrics; facilitating treatment; etc.) can include applying one or more artificial intelligence approaches (e.g., machine learning approaches, etc.) including any one or more of: supervised learning (e.g., using logistic regression, using back propagation neural networks, using random forests, decision trees, etc.), unsupervised learning (e.g., using an Apriori algorithm, using K-means clustering), semi-supervised learning, a deep learning algorithm (e.g., neural networks, a restricted Boltzmann machine, a deep belief network method, a convolutional neural network method, a recurrent neural network method, stacked auto-encoder method, etc.), reinforcement learning (e.g., using a Q-learning algorithm, using temporal difference learning), a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naive Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a dimensionality reduction method (e.g., principal component analysis, partial lest squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and/or any suitable artificial intelligence approach.

However, facilitating characterization of the one or more conditions S150 can be performed in any suitable manner.

2.7 Facilitating Treatment.

Additionally or alternatively, embodiments of the method 100 can include facilitating treatment S160 (e.g., based on one or more abundance metrics; based on one or more characterizations of one or more conditions; etc.), which can function to leverage abundance data to determine, provide, administer, promote, recommend, and/or otherwise facilitate treatment provision (e.g. personalized treatment provision, etc.) for one or more conditions. Facilitating treatment can include applying any suitable techniques associated with analyzing abundance metrics (e.g., for facilitating one or more characterizations; using similar or different statistical operations or algorithms; using the same or different abundance metrics, supplementary data, other suitable data; etc.). Treatments can include any one or more of: therapeutic compositions (e.g., pregnancy-related compositions, medication-based treatments, probiotic-based treatments, topical-based treatments, etc.), surgical treatments, medical device-based treatments, health-related notifications (e.g., transmitted to the subject, to a care provider, etc.) including condition-related and/or treatment-related information derived based on the abundance metrics; diet-related treatments; cognitive/behavioral treatments; physical therapies; clinical-related treatments (e.g., telemedicine, scheduling a care provider appointment, etc.); alternative medicine-based treatments; environmental-based treatments; and/or any other suitable type of treatments. However, facilitating treatment S160 can be performed in any suitable manner.

2.8 Validating.

Figure 10:
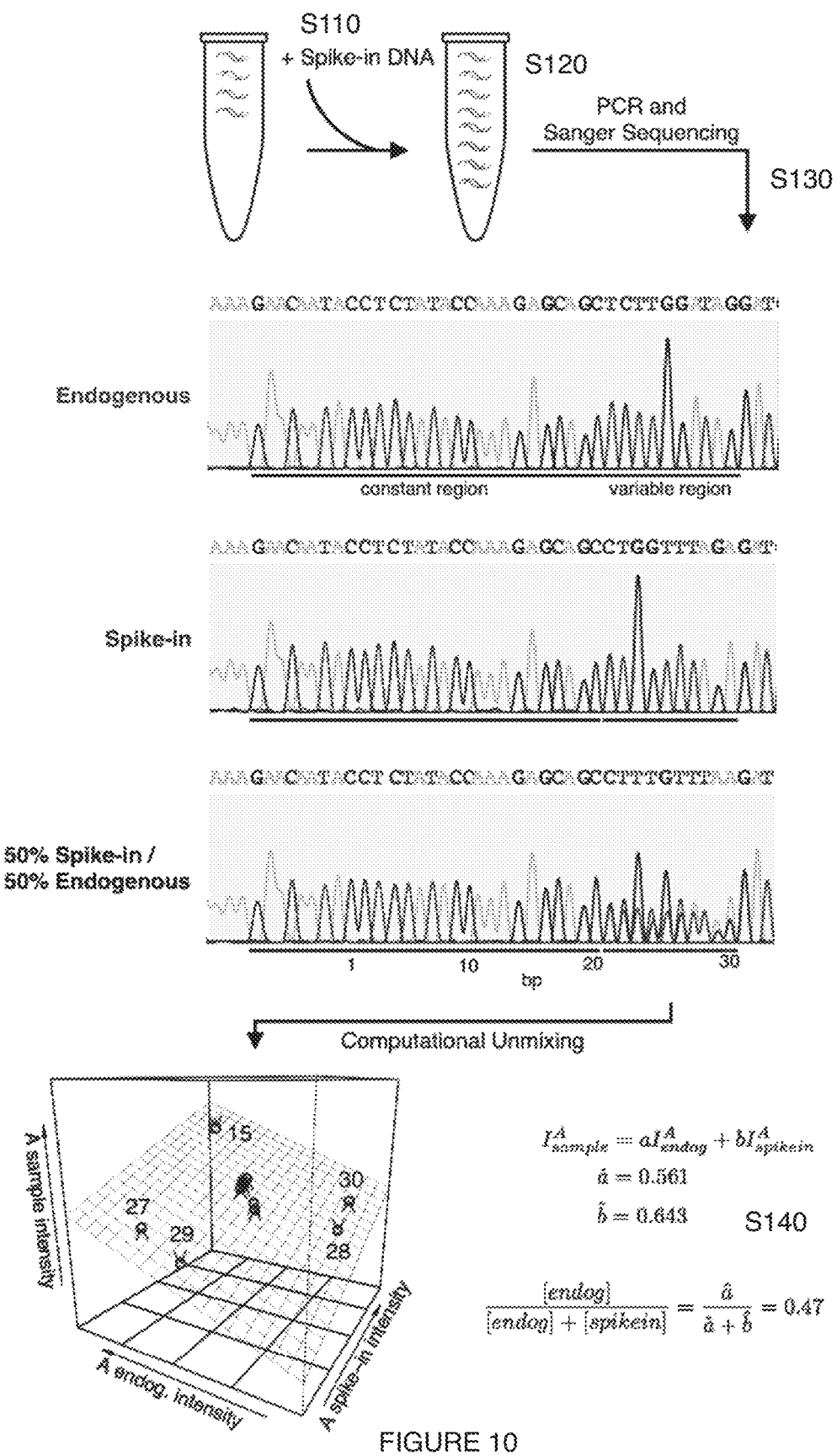
FIG. 10 includes graphical representations of portions of a variation of an embodiment of a method (specific example of Endogenous=SEQ ID NO: 8; specific example of Spike-in =SEQ ID NO: 9; specific example of 50% Spike-in/50% Endogenous=SEQ ID NO: 10)

Additionally or alternatively, embodiments of the method 100 can include validating S105 (e.g., such as validating one or more portions of embodiments of the method 100 and/or system 200, etc.), which can function to evaluate any suitable parameters (e.g., accuracy, cost, efficacy, deployability, etc.) associated with embodiments of the method 100 and/or system 200. In a specific example, FIG. 10 can include a representation a wet-lab protocol of adding spike-in DNA to a sample of unknown mass; where the spike-in DNA sequence is identical to the endogenous DNA, except for a 10 bp variable region; where the spike-in and endogenous DNA is then amplified by PCR, and the resulting amplicon is purified and Sanger sequenced such as using BigDye v3.3 chemistry; where FIG. 10 includes chromatograms of spike-in and endogenous DNA, pure preparations of the endogenous and spike-in DNA individually sequenced; where the chromatogram of a endogenous/spike-in mixture is a linear combination of the pure spike-in and endogenous chromatograms; where FIG. 10 includes results of computational analysis of chromatogram data for calculating endogenous DNA mass; where the proportion of spike-in and endogenous DNA is determined from a linear regression analysis; where each channel of the Sanger chromatogram, corresponding to fluorescently labelled dideoxynucleotides, is individually analyzed; where the analysis on the "A" channel is depicted; and where the peak intensities at the base positions expected to display an "A" peak in either the endogenous or spike-in are measured for the chromatograms. In a specific example, as shown in FIG. 10, validating can include performing sample processing and computational processing (e.g., using any suitable techniques described herein, etc.), in order to evaluate accuracy for embodiments of the method 100 in determining abundance metrics for spike-in mixtures and/or other suitable components; where validation metrics (e.g., proportion of endogenous to spike-in for a spike-in mixture including components of known abundances, etc.) can be calculated in a manner that can be used as a calibration factor for adjusting abundance ratio metrics calculated for samples with unknown target molecule abundances, and/or can be used for any suitable purposes.

Figure 12A:
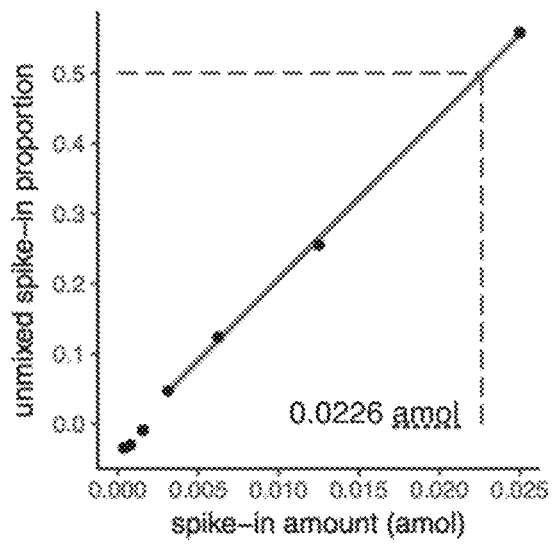
FIGS. 12A-12B include graphical representations of results from validating portions of a variation of an embodiment of a method.
Figure 12B:
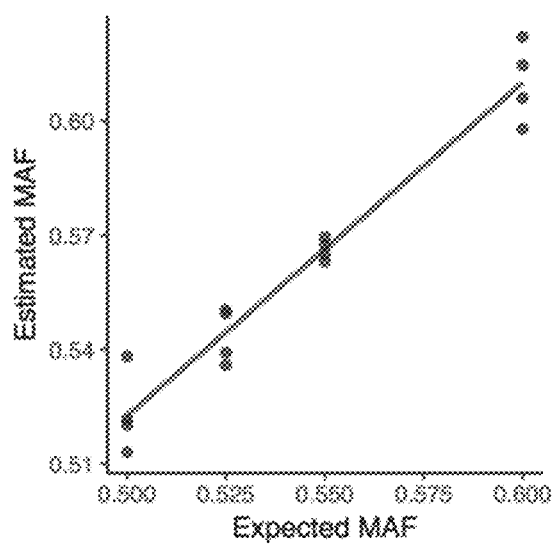

In a variation, as shown in FIGS. 12A-12B, any suitable abundances (e.g., from a serial dilution, etc.) of target-associated molecules (e.g., spike-in molecules) can be used to evaluate accuracy, precision, and/or other suitable parameters associated with portions of embodiments of the method 100. In a specific example, as shown in FIGS. 12A-12B (e.g., indicating the accuracy and/or precision of applying portions of embodiments of the method 100), 42 ng of NA12878 human genomic DNA was mixed with varying amounts of spike-in DNA and amplified with 30 rounds of PCR, and the proportion of spike-in DNA in each sample was determined by applying portions of embodiments of the method 100; and where the regression line was fit to the 4 samples that yielded spike-in proportion >0, and based on the regression fit, 0.0226 amol, or 44.9 ng, is predicted to yield a spike-in proportion of W; where 1 fmol of reference DNA was mixed with spike-in DNA at the indicated proportions; and where mixtures were amplified for 20×PCR, purified, and portions of embodiments of the method 100 can be performed.

However, validation S105 can be performed in any suitable manner.

However, embodiments of the method 100 can be performed in any suitable manner.

Embodiments of the method 100 and/or system 200 can include every combination and permutation of the various system components and the various method processes, including any variants (e.g., embodiments, variations, examples, specific examples, figures, etc.), where portions of embodiments of the method 100 and/or processes described herein can be performed asynchronously (e.g., sequentially), concurrently (e.g., in parallel), or in any other suitable order by and/or using one or more instances, elements, components of, and/or other aspects of the system 200 and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the method 100 and/or system 200 can be embodied and/or implemented at least in part as a machine configured to receive a computer-readable medium storing computer-readable instructions. The instructions can be executed by computer-executable components that can be integrated with embodiments of the system 200. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the method 100, system 200, and/or variants without departing from the scope defined in the claims.

We claim:

1. A method for facilitating prenatal diagnosis of a genetic disorder from a maternal sample associated with a pregnant woman, the method comprising:

generating a first set of target-associated molecules comprising a first target-associated sequence comprising:

a first target-associated region having a nucleotide sequence matching a first target sequence region of a first target sequence of a biological target, wherein the biological target is associated with the genetic disorder; and a target variation region having a nucleotide sequence that differs from a sequence region of the target sequence, the target variation region comprising one or more of an insertion or a deletion resulting in shifted alignment positions for corresponding base pairs of a sequence of the target-associated molecule and the first target sequence;

generating a co-amplified spike-in mixture based on co-amplifying the first set of target-associated molecules and first nucleic acid molecules from the maternal sample to generate amplified nucleic acid fragments, wherein the first nucleic acid molecules comprise the target sequence region;

performing a sequencing operation on the amplified nucleic acid fragments in the co-amplified spike-in mixture to determine at least one chromatogram-related output comprising a first peak associated with the first set of target-associated molecules and a second peak associated with the biological target;

determining a first set of target-associated abundance metrics based on the at least one chromatogram-related output, wherein each target-associated abundance metric, of the first set of target-associated abundance metrics, corresponds to a ratio between the peak intensity metrics of the first peak associated with the first set of target-associated molecules and the second peak associated with the biological target;

determining an overall target-associated abundance metric based on the first set of target-associated abundance metrics; and facilitating the prenatal diagnosis of the genetic disorder based on a comparison between the overall target-associated abundance metric and a reference-associated overall abundance metric describing abundance of a biological reference relative to reference-associated molecules.

2. The method of claim 1, wherein the amplified nucleic acid fragments cover base positions for bases of target-associated sequences, target sequences, reference-associated molecule sequences, and reference sequences, or a combination thereof.

3. The method of claim 1, wherein the sequencing operation comprises analysis of the amplified nucleic acid fragments through capillary gel electrophoresis.

4. The method of claim 1, wherein the sequencing operation comprises detection of fluorescently labelled nucleic acids.

5. The method of claim 1,
wherein the genetic disorder comprises at least one of a chromosomal abnormality and a single gene disorder,
wherein the first target sequence region is associated with at least one of a first chromosome and a mutation,
wherein a reference sequence region of the biological reference is associated with at least one of a second chromosome and a lack of the mutation, and
wherein facilitating the prenatal diagnosis of the genetic disorder comprises facilitating the prenatal diagnosis of the at least one of the chromosomal abnormality and the single gene disorder based on the comparison between the overall target-associated abundance metric and the reference-associated overall abundance metric.

6. The method of claim 5, wherein the genetic disorder comprises the chromosomal abnormality, wherein the first target sequence corresponds to a first loci of the first chromosome, wherein the method further comprises:

generating a second set of target-associated molecules comprising a second target-associated sequence, wherein the second target-associated sequence comprises:
a second target-associated region having a nucleotide sequence matching a second target sequence region of a second target sequence,
wherein the second target sequence corresponds to a second loci of the first chromosome;
wherein the second set of target-associated molecules are co-amplified with the spike-in mixture comprising the first set of target-associated molecules and the first nucleic acid molecules from the maternal sample to generate a second set of amplified nucleic acid fragments;
performing a sequencing operation on the second set of amplified nucleic acid fragments from the co-amplified spike-in mixture to determine at least one chromatogram-related output comprising a third peak associated with the second set of target-associated molecules and a fourth peak associated with the biological target;
determining a second set of target-associated abundance metrics based on the at least one chromatogram-related output, wherein each target-associated abundance metric, of the second set of target-associated abundance metrics, corresponds to a ratio between the peak intensity metrics of the third peak associated with the second set of target-associated molecules and the fourth peak associated with the biological target,
wherein determining the overall target-associated abundance metric comprises determining the overall target-associated abundance metric based on the first set of target-associated abundance metrics and the second set of target-associated abundance metrics, and
wherein the reference sequence region of the biological reference is associated with the second chromosome.

7. The method of claim 1, wherein facilitating the prenatal diagnosis comprises facilitating the prenatal diagnosis of the genetic disorder based on a fetal fraction measurement, the overall target-associated abundance metric, and the reference-associated overall abundance metric.

8. The method of claim 1, further comprising adding at least one sequence repeat to at least one of the first set of target-associated molecules and the first nucleic acid molecules, wherein adding the at least one sequence repeat comprises co-amplifying, with a set of primers comprising a hairpin sequence, the first set of target-associated molecules and the first nucleic acid molecules.

9. A method for biological target quantification from a sample comprising target molecules, the method comprising:

performing a sequencing operation on a first set of target-associated nucleic acid molecules and a set of target nucleic acid molecules, wherein the first set of target-associated molecules comprises a first target-associated sequence comprising:
a first target-associated region having a nucleotide sequence matching a first target sequence region of a first target sequence of a biological target, wherein the set of target molecules comprises the first target sequence region; and
a target variation region having a nucleotide sequence that differs from a sequence region of the first target sequence, the target variation region comprising one or more of an insertion or a deletion of the target-associated molecule and the first target sequence;
determining, based on the sequencing operation, at least one chromatogram-related output comprising a first peak associated with the target-associated molecules and a second peak associated with the biological target;
determining a first set of target-associated abundance metrics based on the at least one chromatogram-related output, wherein each target-associated abundance metric, of the first set of target-associated abundance metrics, corresponds to a ratio between the peak intensity metrics of the first peak associated with the first set of target-associated molecules and the second peak associated with the biological target; and
determining a first overall abundance metric describing a first abundance of the biological target for the sample, based on the first set of target-associated abundance metrics.

10. The method of claim 9, wherein the first set of target-associated nucleic acid molecules and the set of target nucleic acid molecules cover base positions for bases of target-associated sequences, target sequences, reference-associated molecule sequences, and reference sequences, or a combination thereof.

11. The method of claim 9, wherein the sequencing operation comprises analysis of the first set of target-associated nucleic acid molecules and the set of target nucleic acid molecules through capillary gel electrophoresis.

12. The method of claim 9, wherein the sequencing operation comprises detection of labelled bases.

13. The method of claim 9, wherein the biological target is associated with a medical condition, and wherein the method further comprises facilitating characterization of the medical condition based on a first comparison between the first overall abundance metric and an overall reference-associated abundance metric describing abundance of a biological reference.

14. The method of claim 13,
wherein the medical condition comprises at least one of a single gene disorder and a cancer condition,
wherein the first overall abundance metric is associated with a first time period,
wherein the method further comprises determining a second overall abundance metric describing a second abundance of the biological target, wherein the second overall abundance metric is associated with a second time period, and
wherein facilitating the characterization of the medical condition comprises facilitating the characterization of the medical condition based on the first comparison and the second overall abundance metric.

15. The method of claim 9,
wherein determining the at least one chromatogram-related output comprises determining the at least one chromatogram-related output based on the sequencing operation associated with the first set of target-associated molecules, the set of target molecules, and a second set of target-associated molecules,
wherein the second set of target-associated molecules comprises a second target-associated sequence comprising a second target-associated region having a nucleotide sequence matching a second target sequence region of a second target sequence,
wherein the method further comprises determining a second set of target-associated abundance metrics based on the at least one chromatogram-related output, wherein each target-associated abundance metric, of the second set of target-associated abundance metrics, corresponds to a ratio between the peak intensity metrics of the third peak associated with the second set of target-associated molecules and the fourth peak associated with the biological target, and
wherein determining the first overall abundance metric is based on the first set of target-associated abundance metrics and the second set of target-associated abundance metrics.

16. The method of claim 15, wherein the first target sequence corresponds to a first loci of a chromosome, wherein the second target sequence corresponds to a second loci of the chromosome, and wherein the method further comprises facilitating characterization of a chromosomal abnormality based on the first overall abundance metric.

17. The method of claim 1, wherein the sequencing operation comprises laser detection of labelled nucleic acids.

18. The method of claim 9, wherein the sequencing operation comprises laser detection of labelled nucleic acids.

* * * * *